US007842013B2

(12) United States Patent
Haberland et al.

(10) Patent No.: US 7,842,013 B2
(45) Date of Patent: Nov. 30, 2010

(54) TROCAR AND CANNULA ASSEMBLY HAVING CONICAL VALVE AND RELATED METHODS

(75) Inventors: Gary W. Haberland, Oviedo, FL (US); Brent Van Camp, Kemersville, NC (US); Michael Benner, Sanford, FL (US); Derrell James, Sanford, FL (US)

(73) Assignee: Genico, Inc., Winter Park, FL (US)

( * ) Notice: Subject to any disclaimer, the term of this patent is extended or adjusted under 35 U.S.C. 154(b) by 625 days.

(21) Appl. No.: 11/807,202

(22) Filed: May 25, 2007

(65) Prior Publication Data

US 2008/0033363 A1 Feb. 7, 2008

Related U.S. Application Data

(63) Continuation-in-part of application No. 11/503,314, filed on Aug. 15, 2006, now Pat. No. 7,585,288, which is a continuation-in-part of application No. 11/153,860, filed on Jun. 15, 2005, now abandoned, which is a continuation-in-part of application No. 10/879,644, filed on Jun. 29, 2004, now abandoned, which is a continuation of application No. 10/763,762, filed on Jan. 23, 2004, now abandoned.

(51) Int. Cl.
*A61M 5/178* (2006.01)
*A61B 17/34* (2006.01)

(52) U.S. Cl. .............................. 604/167.03; 604/167.01; 606/185

(58) Field of Classification Search ................................
604/167.01–167.04, 256; 606/185
See application file for complete search history.

(56) References Cited

U.S. PATENT DOCUMENTS 3,939,835 A 2/1976 Bridgman 4,056,116 A 11/1977 Carter et al.
4,486,024 A 12/1984 Cooper (Continued)

FOREIGN PATENT DOCUMENTS

| EP | 0066008 A2 | 1/1985 |
|---|---|---|
| EP | 0131349 A1 | 1/1985 |
| EP | 0617924 A2 | 10/1994 |

OTHER PUBLICATIONS

[author unknown] *Applied Universal® Seal Technology*, Applied Medical © 2003.

(Continued)

*Primary Examiner*—Nicholas D Lucchesi
*Assistant Examiner*—Ian K Holloway
(74) *Attorney, Agent, or Firm*—Innovative IP, PLC; Sandra M. Sovinski

(57) ABSTRACT

A trocar system for endoscopic surgery, cap assembly, and related methods are provided. The cap assembly includes a valve housing with an opening formed in line with an axis of the valve housing and also includes a valve positioned adjacent the opening of the valve housing. The valve body includes a proximal valve section including a valve ring positioned within the valve housing, and a distal valve section extending axially from the proximal valve section. The distal valve section includes a valve extension having a proximal and distal end portions, and a substantially conically shaped medial portion connected to and extending therebetween, wherein a plurality of friction-reduction features, preferably tear-drop shaped knobs, are disposed proximate the distal end portion and extending a distance in the medial portion of the valve. A valve opening is positioned in the distal end portion of the valve extension, adapted to individually and separately receive the elongate tools so that when any one of the elongate tools of varying diameter is positioned therethrough, electrostatic adhesion between the valve and the tool is minimized and a seal is maintained between peripheries of the valve extension surrounding the valve opening and outer peripheries of the inserted elongate tool.

14 Claims, 15 Drawing Sheets

U.S. PATENT DOCUMENTS

| | | |
|---|---|---|
| 4,493,319 A | 1/1985 | Polk et al. |
| 4,723,550 A | 2/1988 | Bales et al. |
| 4,842,591 A | 6/1989 | Luther |
| 4,943,280 A | 7/1990 | Lander |
| 4,960,412 A | 10/1990 | Fink |
| 5,104,383 A | 4/1992 | Shichman |
| 5,125,553 A | 6/1992 | Oddsen et al. |
| 5,127,909 A | 7/1992 | Shichman |
| 5,141,498 A | 8/1992 | Christian |
| 5,150,702 A | 9/1992 | Miyanaga et al. |
| 5,167,636 A | 12/1992 | Clement |
| 5,194,383 A | 3/1993 | Tsai et al. |
| 5,197,955 A | 3/1993 | Stephens et al. |
| 5,209,737 A | 5/1993 | Ritchart et al. |
| 5,217,468 A | 6/1993 | Clement |
| 5,220,928 A | 6/1993 | Oddsen et al. |
| 5,226,891 A | 7/1993 | Bushatz et al. |
| 5,250,065 A | 10/1993 | Clement et al. |
| 5,251,873 A | 10/1993 | Atkinson et al. |
| 5,282,790 A | 2/1994 | Clement |
| 5,295,657 A | 3/1994 | Atkinson |
| 5,295,658 A | 3/1994 | Atkinson et al. |
| 5,300,035 A | 4/1994 | Clement |
| 5,300,036 A | 4/1994 | Mueller et al. |
| 5,306,237 A | 4/1994 | Clement et al. |
| 5,308,336 A | 5/1994 | Hart et al. |
| 5,312,351 A | 5/1994 | Gerrone |
| 5,312,363 A | 5/1994 | Ryan et al. |
| 5,320,608 A | 6/1994 | Gerrone |
| 5,334,164 A | 8/1994 | Guy et al. |
| 5,335,671 A | 8/1994 | Clement |
| 5,338,292 A | 8/1994 | Clement et al. |
| 5,342,315 A | 8/1994 | Rowe et al. |
| 5,344,420 A | 9/1994 | Hilal et al. |
| 5,350,364 A | 9/1994 | Stephens et al. |
| 5,360,417 A | 11/1994 | Gravener et al. |
| 5,366,478 A | 11/1994 | Brinkerhoff et al. |
| 5,374,244 A | 12/1994 | Clement et al. |
| 5,376,077 A | 12/1994 | Gomringer |
| 5,385,553 A | 1/1995 | Hart et al. |
| 5,389,081 A | 2/1995 | Castro |
| 5,397,335 A | 3/1995 | Gresl et al. |
| 5,402,982 A | 4/1995 | Atkinson et al. |
| 5,407,433 A | 4/1995 | Loomas |
| 5,409,013 A | 4/1995 | Clement |
| 5,411,483 A | 5/1995 | Loomas et al. |
| 5,437,646 A | 8/1995 | Hunt et al. |
| 5,443,452 A | 8/1995 | Hart et al. |
| 5,449,141 A | 9/1995 | Gillett et al. |
| 5,476,475 A | 12/1995 | Gadberry |
| 5,496,280 A | 3/1996 | Vandenbroek et al. |
| 5,497,433 A | 3/1996 | Itoh et al. |
| 5,501,426 A | 3/1996 | Atkinson et al. |
| 5,505,210 A | 4/1996 | Clement |
| 5,533,708 A | 7/1996 | Atkinson et al. |
| 5,542,931 A | 8/1996 | Gravener et al. |
| 5,549,565 A | 8/1996 | Ryan et al. |
| 5,569,205 A | 10/1996 | Hart et al. |
| 5,584,850 A | 12/1996 | Hart et al. |
| 5,603,702 A * | 2/1997 | Smith et al. .................. 604/256 |
| 5,628,732 A | 5/1997 | Antoon, Jr. et al. |
| 5,634,908 A | 6/1997 | Loomas |
| 5,643,282 A | 7/1997 | Kieturakis |
| 5,651,771 A | 7/1997 | Tangherlini et al. |
| 5,657,963 A | 8/1997 | Hinchliffe et al. |
| 5,662,615 A | 9/1997 | Blake, III |
| 5,693,031 A | 12/1997 | Ryan et al. |
| 5,709,664 A | 1/1998 | Vandenbroek et al. |
| 5,720,730 A | 2/1998 | Blake, III |
| 5,722,958 A | 3/1998 | Gravener et al. |
| 5,727,770 A | 3/1998 | Dennis |
| 5,752,938 A | 5/1998 | Flatland et al. |
| 5,782,812 A | 7/1998 | Hart et al. |
| 5,792,112 A | 8/1998 | Hart et al. |
| 5,792,113 A | 8/1998 | Kramer et al. |
| 5,797,907 A | 8/1998 | Clement |
| 5,803,919 A | 9/1998 | Hart et al. |
| 5,820,600 A * | 10/1998 | Carlson et al. ......... 604/167.03 |
| 5,827,228 A | 10/1998 | Rowe |
| 5,865,807 A | 2/1999 | Blake, III |
| 5,871,471 A | 2/1999 | Ryan et al. |
| 5,895,377 A | 4/1999 | Smith et al. |
| 5,980,493 A | 11/1999 | Smith et al. |
| 5,984,919 A | 11/1999 | Hilal et al. |
| 5,989,224 A | 11/1999 | Exline et al. |
| 6,039,302 A | 3/2000 | Cote, Sr. et al. |
| RE36,702 E | 5/2000 | Green et al. |
| D426,635 S | 6/2000 | Haberland et al. |
| 6,093,176 A * | 7/2000 | Dennis ....................... 604/256 |
| 6,099,505 A | 8/2000 | Ryan et al. |
| 6,162,196 A | 12/2000 | Hart et al. |
| 6,193,672 B1 | 2/2001 | Clement |
| 6,217,555 B1 | 4/2001 | Hart et al. |
| 6,228,061 B1 | 5/2001 | Flatland et al. |
| 6,258,065 B1 | 7/2001 | Dennis et al. |
| D449,887 S | 10/2001 | Haberland et al. |
| 6,344,038 B1 | 2/2002 | Weber |
| 6,355,028 B2 | 3/2002 | Castaneda et al. |
| 6,432,085 B1 | 8/2002 | Stellon et al. |
| 6,482,181 B1 | 11/2002 | Racenet et al. |
| 6,500,170 B2 | 12/2002 | Palmer et al. |
| 6,503,245 B2 | 1/2003 | Palmer et al. |
| 6,551,282 B1 | 4/2003 | Exline et al. |
| 6,554,823 B2 | 4/2003 | Palmer et al. |
| 6,569,119 B1 | 5/2003 | Haberland et al. |
| 6,588,428 B2 | 7/2003 | Shikani et al. |
| 6,595,946 B1 | 7/2003 | Pasqualucci et al. |
| 6,612,196 B1 | 9/2003 | Petzold |
| 6,702,787 B2 * | 3/2004 | Pasqualucci et al. ......... 604/256 |
| 6,723,073 B2 | 4/2004 | Ley et al. |
| 6,945,983 B2 | 9/2005 | Dittrich et al. |
| 6,958,069 B2 | 10/2005 | Shipp et al. |
| 7,025,747 B2 * | 4/2006 | Smith .................... 604/167.06 |
| 7,041,055 B2 | 5/2006 | Young et al. |
| 7,077,865 B2 | 7/2006 | Bao et al. |
| 7,100,890 B2 | 9/2006 | Cote et al. |
| 7,214,228 B2 | 5/2007 | Crabtree |
| 7,217,275 B2 | 5/2007 | Crabtree |
| 2002/0013556 A1 | 1/2002 | Cote et al. |
| 2003/0216770 A1 | 11/2003 | Persidsky et al. |
| 2004/0138626 A1 | 7/2004 | Cote et al. |
| 2004/0215107 A1 | 10/2004 | Sarstedt et al. |
| 2004/0254541 A1 | 12/2004 | Wong et al. |
| 2005/0033342 A1 | 2/2005 | Hart et al. |
| 2005/0070946 A1 * | 3/2005 | Franer et al. ................. 606/185 |
| 2005/0256461 A1 | 11/2005 | DiFiore et al. |
| 2006/0025781 A1 | 2/2006 | Young et al. |
| 2006/0047293 A1 | 3/2006 | Haberland et al. |
| 2006/0229565 A1 * | 10/2006 | Dennis et al. ........... 604/167.03 |
| 2007/0185453 A1 * | 8/2007 | Michael et al. ......... 604/164.01 |

OTHER PUBLICATIONS

[author unknown] *Modular Laparoscopic Instruments*, 2003 GeniCon U.S.A. L.C.
[author unknown] *Trocar & Cannula Systems* 2003, GeniCon U.S.A. L.C.
[author unknown] *Applied Universal ® Seal Technology*, Applied Medical © Jan. 1999.
[author unknown] *Modular Laparoscopic Instruments*, Jan. 1999, GeniCon U.S.A. L.C.
[author unknown] *Trocar and Cannula Systems*, Jan. 1999, GeniCon U.S.A. L.C.

* cited by examiner

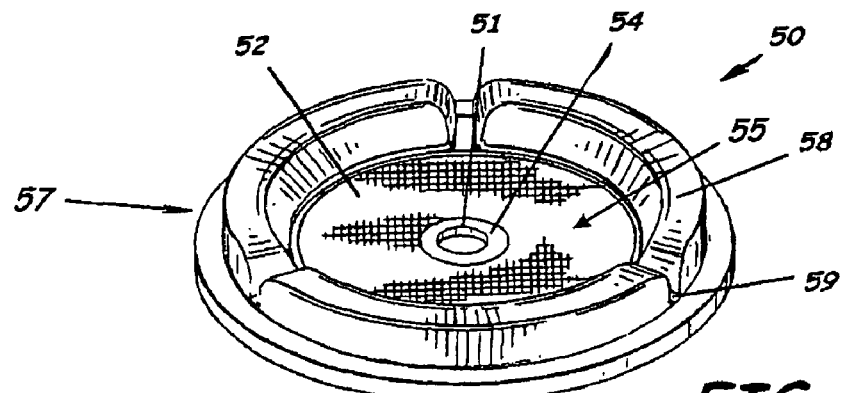
FIG. 6.
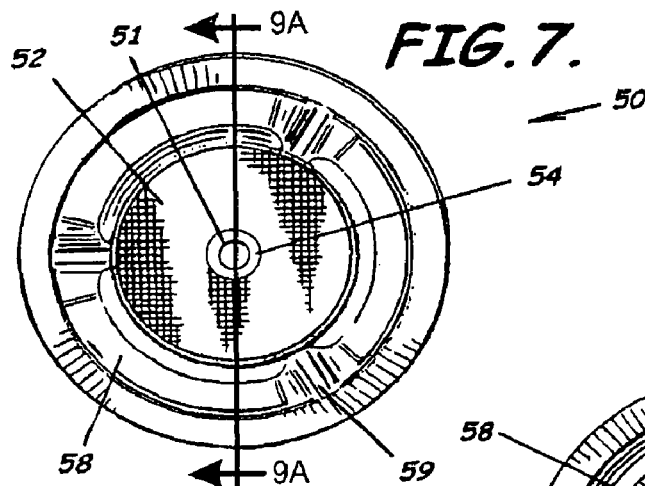
FIG. 7.
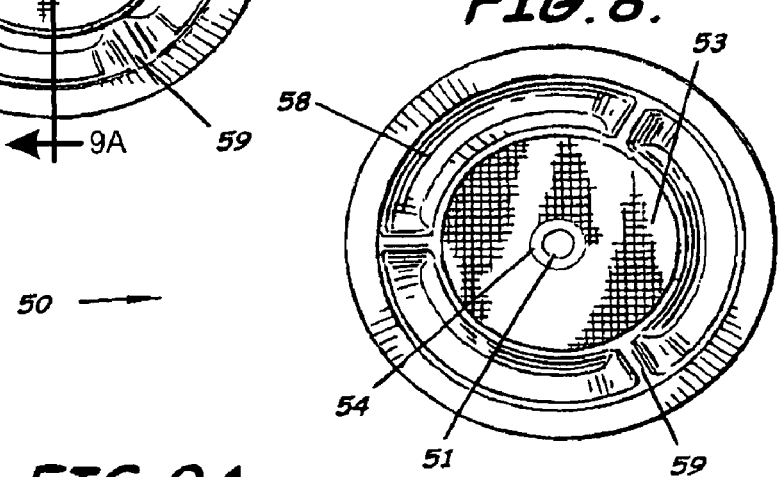
FIG. 8.
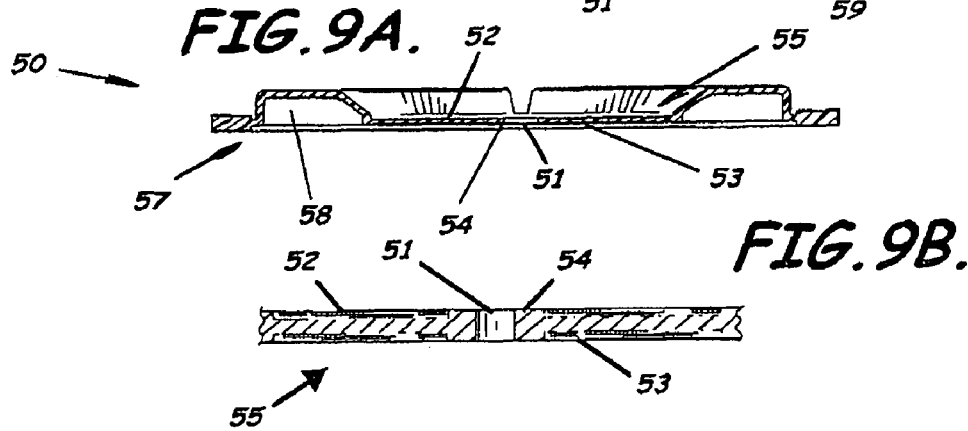
FIG. 9A.
FIG. 9B.

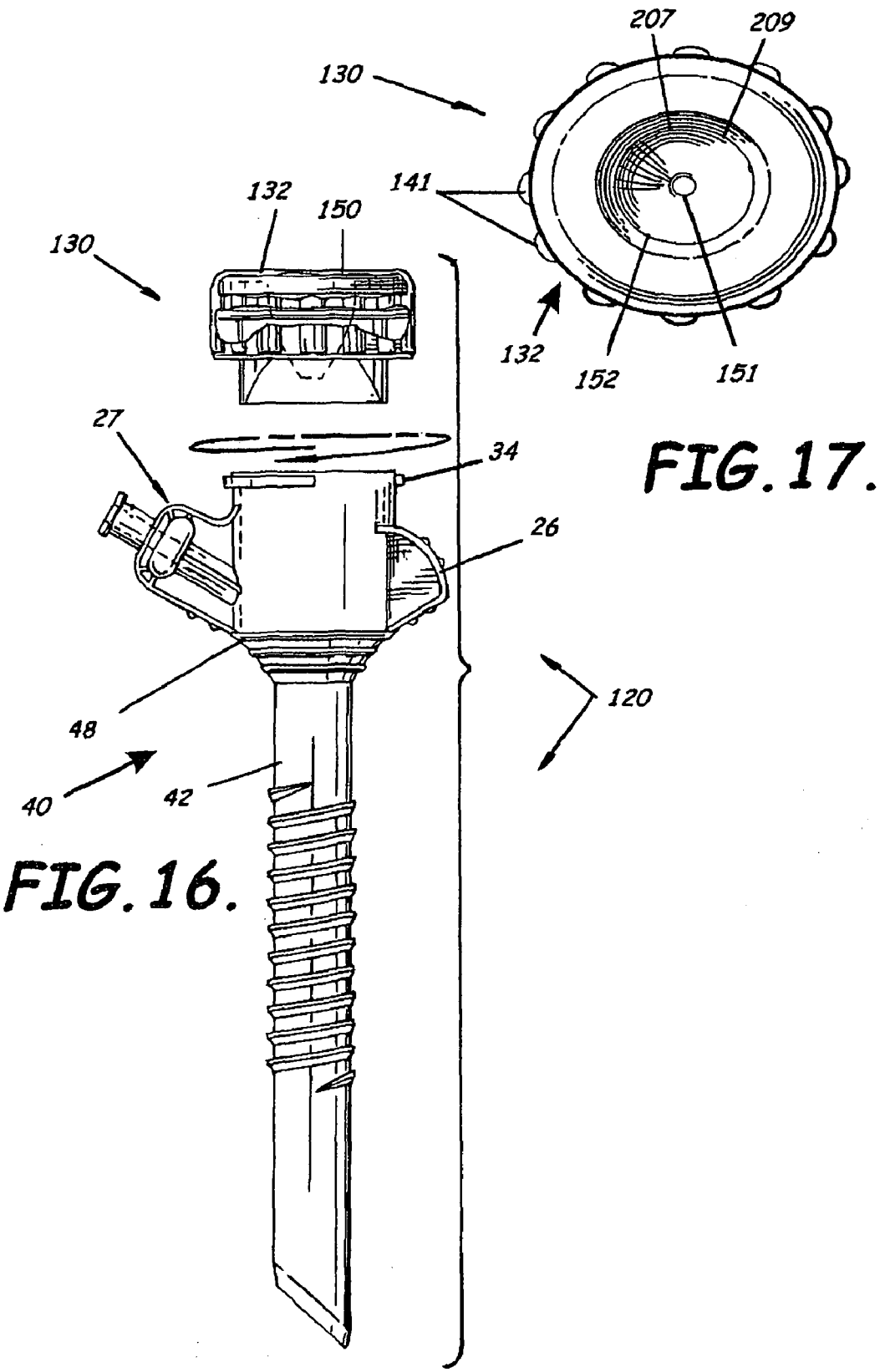

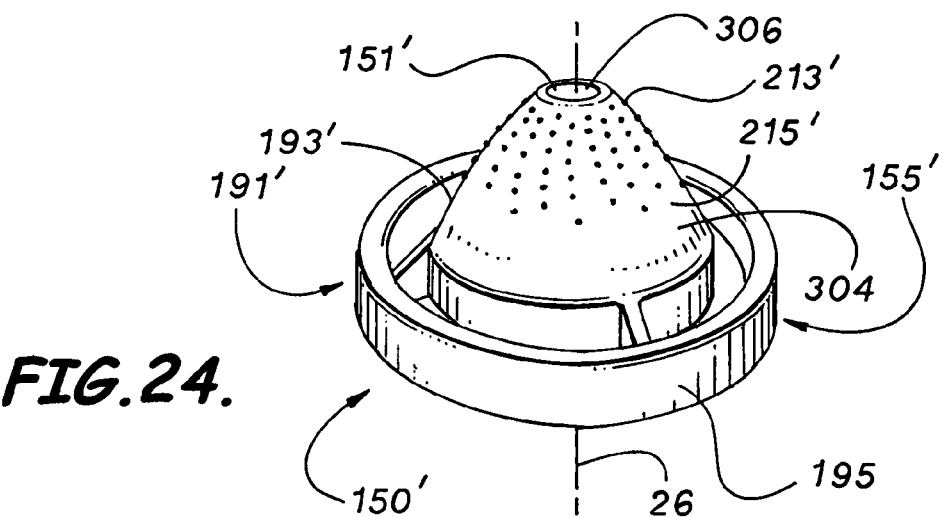
FIG. 24.
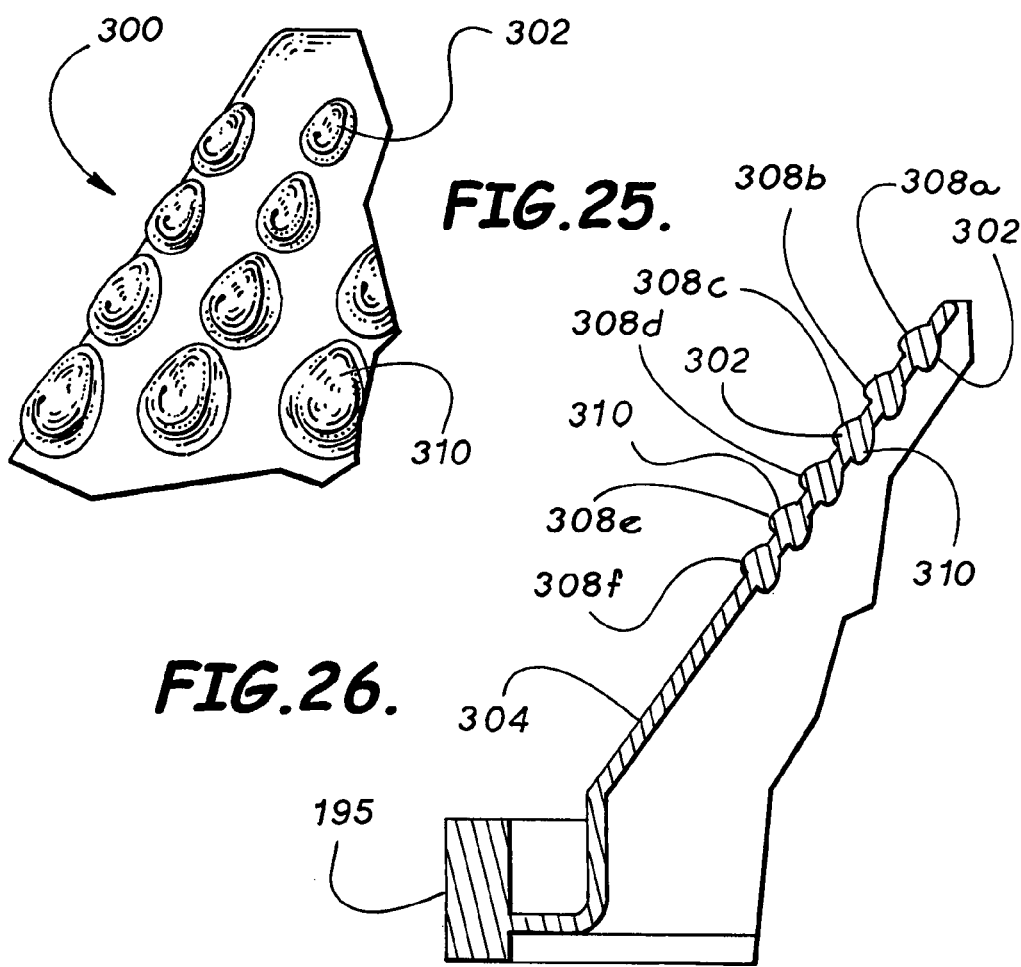
FIG. 25.
FIG. 26.

TROCAR AND CANNULA ASSEMBLY HAVING CONICAL VALVE AND RELATED METHODS

CROSS-REFERENCE TO RELATED APPLICATION

The present U.S. Non-Provisional patent application cross-references and claims priority and benefit as a continuation-in-part of co-pending U.S. patent application Ser. No. 11/503,314, filed Aug. 15, 2006 now U.S. Pat. No. 7,585,288, entitled "Trocar and Cannula Assembly Having Conical Valve and Related Methods," which is a continuation-in-part of co-pending U.S. patent application Ser. No. 11/153,860, filed Jun. 15, 2005 now abandoned, which is a continuation-in-part of co-pending U.S. patent application Ser. No. 10/879,644 filed Jun. 29, 2004 now abandoned, which was a continuation of, and claimed the benefit of U.S. patent application Ser. No. 10/763,762 filed on Jan. 23, 2004, now abandoned, each of which is hereby incorporated by reference in its entirety.

FIELD OF THE INVENTION

The present invention relates in general to the field of medical devices. More particularly, the present invention relates to trocar systems, cannulas, valves, and methods related thereto.

BACKGROUND OF THE INVENTION

Trocar systems have been developed over the years for various endoscopic applications in the field of medicine. These trocar systems conventionally include a cannula through which a trocar or obturator or other endoscopic related tool extends. It is known to use one or more valves positioned within or connected to a proximal end of the cannula of a trocar system. Known devices having one or more valves can be bulky and awkward to use and have complex multi-component mechanical valves which can be difficult and expensive to manufacture and can have an increased risk of mechanical failure. The mechanical valves also have little or no flexibility.

Other trocar systems have been developed which are easier to use and have less complex mechanical valves. One example of such trocar system can be seen in U.S. Pat. No. 6,569,119 by Haberland et al. titled "Trocar System Having Cannula with Finger Grips." These devices provide enhanced gripping and easier handling of the systems. Nevertheless, there is also still a need for alternative cannula and valve configurations for trocar systems, a need for relatively less expensive trocar systems, a need for trocar systems with better performance, a need for more flexible trocar systems and valves which enhance handling thereof by medical personnel users, i.e., physicians, and yet are still effective for various endoscopic surgical procedures.

SUMMARY OF THE INVENTION

With the foregoing in mind, embodiments of the present invention advantageously provide embodiments of a valve having a unique design to provide a secured seal around a plurality of tools that individually and separately extend through the valve. Embodiments of a valve provide an easier insertion and retraction, of various laparoscopic surgical instruments as well as other surgically related items which have varying diameters, wherein the present invention advantageously accepts a broad range thereof, such as diameters from 5 mm to 15 mm. Further, problematical instruments do not get obstructed or caught in a multi-component valve assembly as disclosed. Embodiments of the present invention also advantageously provide a trocar system having relatively low costs associated with the manufacturing of components of the system, e.g., valves, and thereby can reduce the cost associated with the trocar system.

Embodiments of the present invention additionally advantageously provide a more flexible trocar system which is effective during various endoscopic surgical procedures. Embodiments of the present invention further advantageously provide enhanced methods of forming a seal around tools and of using a trocar system during surgical procedures.

Still further, because embodiments of a valve can have a relatively flat and thin provile and because peripheries of a valve are fixedly connected to a valve housing, the valve advantageously can operate like a membrane. Furthermore, because various types and diameters of tools can be used by medical personnel, embodiments of a valve advantageously allow one type of valve, cannula, or trocar system to be readily used for all of these various sizes and types of tools. Moreover, embodiments of the present invention further provide a valve having advantageous anti-friction features that facilitate insertion and removal of instruments therethrough.

More particularly, a trocar system includes, but is not limited to, a cannula having an elongate cannula body. The cannula body has medial and distal portions thereof having at least a first diameter. The cannula body also has a proximal portion thereof connected to the medial portion and having a second diameter. The second diameter is greater than the first diameter. According to an embodiment of the trocar system, the system also includes a valve housing being readily detachably connected to the proximal portion of the cannula body. The valve housing has an axis and a first opening at a proximal end of the valve housing, a second opening at a distal end of the valve housing, and an axially downward facing shoulder. The first opening is defined by a plurality of sidewalls extending in a substantially axial direction, and has a first opening diameter.

According to embodiments of the present invention, the trocar system also includes a cap assembly which includes at least one valve positioned entirely within the valve housing. According to an embodiment of the cap assembly, the at least one valve can include a valve body having an annular-shaped valve opening positioned in a medial portion of the valve body and adapted to individually and separately receive a plurality of different elongate tools. Each of the tools have a different diameter therethrough so that when any one of the plurality of elongate tools is positioned through the valve opening, a septum seal is maintained between peripheries of the valve body surrounding the valve opening and abuttingly contacting outer peripheries of the any one of the plurality of elongate tools extending therethrough. The valve body has first and second layers of a fabric material and a layer of elastomeric material positioned between and contacting each of the first and second layers of the fabric material.

The valve body also has a periphery valve section connected to and extending radially outwardly from peripheries of the valve body. The periphery valve section includes an outer ring with an outer perimeter thereof defining an outer perimeter of the septum valve, the outer ring engaging the axially downward facing shoulder of the valve housing. The periphery valve section has a plurality of rib members each radially extending substantially an entire distance between an outer perimeter of the valve body and the outer perimeter of the periphery valve section and symmetrically positioned spaced-apart from each other. The periphery valve section has a greater flexibility than the valve body.

The trocar system also includes a compression ring positioned in the valve housing adjacent the septum valve. The compression ring compresses the outer ring of the septum valve against the axially downward facing shoulder of the valve housing in order to fixedly position the septum valve within the valve housing. The compression ring has a compression ring opening substantially aligned with the first opening of the valve housing. The trocar system further includes a plurality of tools that each have an elongate body for extending through the valve housing, the valve opening of the at least one valve, and the cannula.

Further more particularly, the cap assembly of the trocar system can include, but is not limited to, a valve housing having at least one opening formed in line with an axis of the valve housing, with the at least one opening being defined by a plurality of sidewalls extending in a substantially axial direction. The cap assembly also includes at least one valve positioned adjacent to the at least one opening of the valve housing. The at least one valve includes a valve body having an annular-shaped valve opening adapted to individually and separately receive a plurality of different elongate tools. Each of the elongate tools can have a different diameter so that when any one of the plurality of elongate tools is positioned through the valve opening, and when the valve is abuttingly contacting outer peripheries of the any one of the plurality of diameter elongate tools extending therethrough, a septum seal is maintained between peripheries of the valve body surrounding the valve opening. The valve body has at least one layer of a fabric material and a layer of elastomeric material. The valve body also has a periphery valve section connected to and extending radially outwardly from peripheries of the valve body. The periphery valve section has a plurality of rib members, each radially extending substantially an entire distance between an outer perimeter of the valve body and an outer perimeter of the periphery valve section.

According to another embodiment of the trocar system, the system can include a valve housing adapted to detachably connect to a cannula and characterized by having a proximal end housing portion, a distal end housing portion, and a medial housing portion connected therebetween having a proximal valve housing inner perimeter surface and a distal valve housing inner perimeter surface which can be of the same or different diameters. The proximal end housing portion can include a first opening having a first opening diameter defined by portions of an inner valve housing sidewall extending distally in a substantially axial direction. The proximal end housing portion can also include an annular valve ring recess adapted to receive an annular valve ring which surrounds the first opening. The distal end housing portion can include a second opening diameter defined by a distal valve housing sidewall extending in a substantially axial direction.

According to an another embodiment of the cap assembly, the at least one valve positioned within a valve housing includes a first valve having a valve body which includes a proximal valve section fixedly positioned within the valve housing and a distal valve section extending axially from the proximal valve section and into the proximal portion of the cannula. The proximal valve section can include a valve ring positioned in the valve ring recess of the valve housing. The valve ring has a proximal surface, a distal surface, an inner perimeter surface, and an outer perimeter surface defining an outer perimeter of the valve body. The proximal valve section of the valve body can also include a plurality of convolutes each having a first sidewall extending radially inwardly from a portion of the inner perimeter surface of the valve ring and a second sidewall extending axially from the first sidewall substantially parallel to the inner perimeter surface of the valve ring and forming an inner radial periphery of the proximal valve section.

The inner perimeter surface of the valve ring, the first sidewall, and the second sidewall of each of the plurality of convolutes form a respective convolute recess for each of the plurality of convolutes. The proximal valve section of the valve body can also include a plurality of rib members each radially extending substantially an entire distance between the inner radial periphery of the proximal valve section and inner perimeter surface of the valve ring and can be symmetrically positioned spaced-apart from each other. The distal valve section of the valve body can include a valve extension extending axially from the plurality of convolutes. The valve extension can include a proximal end portion substantially connected to a distal portion of each of the plurality of convolutes, a distal end portion, and a substantially conically shaped medial portion connected to and extending therebetween. An annular-shaped valve opening is positioned in the distal end portion of the valve extension and is adapted to individually and separately receive therethrough any one of a plurality of different elongate tools each having a different diameter so that when any one of the plurality of elongate tools is positioned through the valve opening, a seal, e.g., septum seal, is maintained between peripheries of the valve extension surrounding the valve opening and outer peripheries of any one of the plurality of elongate tools extending therethrough.

The first valve can also include a compression ring positioned in the valve housing abuttingly contacting an axially facing distal surface of the valve ring to hold the valve ring in the valve ring recess and to compress the valve ring against an axially facing inner surface of the proximal end housing portion of the valve housing adjacent the valve ring recess in order to fixedly position the valve within the valve housing. The compression ring can include a compression ring opening substantially aligned axially with the first opening of the valve housing to allow extension of the plurality of elongate tools therethrough, an outer perimeter surface having a radial diameter sized so that the compression ring substantially abuttingly contacts the distal valve housing inner perimeter surface when positioned within the valve housing, and an annular flange extending into each one of the plurality of convolute recesses to individually and separately engage a corresponding one of the plurality of convolutes to further enhance positioning and securing of the first valve within the valve housing.

The cap assembly can also include a second valve to advantageously help ensure inter-cavity sealing. The second valve can include an annular flange portion spaced axially from the valve ring of the first valve and having a radial diameter sized so that the annular flange portion substantially abuttingly contacts both the distal valve inner housing perimeter surface and an axially facing distal surface of the compression ring adjacent the compression ring opening to enhance positioning of the second valve at least partially within the valve housing. The second valve can also have a second valve opening positioned within the annular flange portion and substantially aligned axially with the first opening of the valve housing to allow extension of the plurality of elongate tools therethrough, an annular-shaped sidewall connected to the annular flange and extending distally in a substantially axial direction when positioned in the valve housing, and a pair of valve flaps connected to and extending inwardly from the annular-shaped sidewall and having at least one slit along common peripheral edges thereof through which the plurality of tools extend individually and separately. The second valve can be held in place through use of a cap seal ring positioned at least partially within the valve housing and positioned to abuttingly contact a distal surface of the annular flange portion of the second valve when the second valve is positioned in the valve housing. The cap seal ring can have an axially extending annular-shaped flange axially spaced apart from the compression ring to provide a slot or recess to releasably receive the annular flange portion of the second valve. The cap seal ring can also include a plurality of radially extending flanges each adapted to engage other peripheries of a separate one of the plurality of radially extending flanges of the cannula to slidably detachably connect the valve housing to the cannula.

Embodiments of the present invention also include methods of using a trocar system. For example, according to embodiment of a method, the method includes the step of providing a cap assembly in a trocar system. The cap assembly has a septum valve including a valve body having an annular-shaped valve opening positioned in a medial portion of the valve body adapted to receive individually and separate a plurality of tools therethrough so that when any one of the plurality of tools is positioned through the valve opening abuttingly contacting outer peripheries of the any one of the plurality of tools extending therethrough, a septum seal is maintained between peripheries of the valve body surrounding the valve opening. The valve body can include first and second layers of fabric material and a layer of elastomeric material positioned between and contacting each of the first and second layers of the fabric material and can include a periphery valve section connected to an extending radially outwardly from peripheries of the valve body and having an outer perimeter thereof adapted to be fixedly connected to the valve housing. The periphery valve section can also have a plurality of rib members each radially extending substantially an entire distance between an outer perimeter of the valve body and the outer perimeter of the periphery valve section and symmetrically positioned spaced-apart from each other. The periphery valve section can have a greater flexibility than the valve body.

The method of using a trocar system can also include the step of inserting a tool through the septum valve and cap assembly comprising the septum valve thereof. During the inserting step, the periphery valve section is deformed temporarily so that the valve body extends distally by contact pressure from the tool and so that a distal end of the tool is guided toward the valve opening and then the periphery valve section is refracted to its selected biased position upon the complete insertion of the tool. The method of using a trocar system can also include the step of guiding the tool to the septum valve with a substantially cylindrical-shaped cap assembly opening when the tool is being inserted through the cap assembly. The method of using a trocar system can further include the steps of extending the tool through a cannula body matingly connected to the cap assembly at a proximal portion thereof, detaching the cap assembly from the proximal portion of the cannula body, and removing tissue or other specimen from the cannula body.

According to another embodiment of the method of using a trocar system, the method can include the step of providing a cap assembly in a trocar system including a valve positioned at least partially within a valve housing. The valve can include a valve body having a proximal valve section positioned within the valve housing and a distal valve section extending axially from the proximal valve section and including a valve extension having a proximal end portion a distal end portion, and a substantially conically shaped medial portion connect to and extending therebetween. A valve opening is positioned in the distal end portion of the valve extension and is adapted to individually and separately receive therethrough any one of a plurality of different elongate tools. The method can also include the step of inserting a tool through the cap assembly including the valve extension and a valve opening thereof, during which the valve extension guides the distal end of the tool to the valve opening and upon reaching the valve opening, the valve opening is deformed temporarily by contact pressure from the tool so that upon the complete insertion of the tool, a seal is formed around outer peripheries of the tool. The method further includes the steps of guiding the tool to the valve extension with a substantially cylindrical-shaped cap assembly opening when the tool is being inserted through the cap assembly, extending the tool through a cannula body matingly connected to the cap assembly at a proximal portion thereof, detaching the cap assembly from the proximal portion of the cannula body, and removing tissue or other specimen from the cannula body.

The preceding valve can also include friction-reduction features to advantageously minimize electrostatic forces between instruments and the valve. A reduction in electrostatic adhesion can be realized from the friction-reduction features, preferably protrusions formed on the inner and outer surfaces of the conically shaped medial portion, proximate the distal end and the valve opening. Kinetic friction between the valve and related instruments is advantageously minimized as the valve opening is deformed temporarily by contact pressure from the tool, wherein contact area between the valve and the instruments is reduced. The friction-reduction features can reduce the resistive forces between the contact surfaces of an inserted instrument and the valve without compromise to the septum seal or to the inherent flexibility and adaptability of the valve of the present invention, wherein a broad endoscopic instrument diameter range, from about 5 mm to 15 mm diameter, can be successfully accepted. The friction-reduction features are preferably defined proximate the apical end of the valve, in anticipation of contact with the plurality of elongate tools extended therethrough, and are further preferably defined on both opposing surfaces in order that advantageous minimization of electrostatic forces may be realized also during contact between the valve body and the second valve.

Embodiments of the present invention also include methods of forming a valve for a trocar system. For example, a method can include providing a slab of an elastomeric material, a first layer of a fabric material overlying the elastomeric material, and a second layer of fabric material underlying the elastomeric material, cutting a disc shape in the slab, compressing the slab so that the elastomeric material extends outwardly from the peripheries of the first and second layers of the fabric material, and curing the compressed slab to form a septum valve for a trocar system.

Another embodiment of the method of forming a valve for a trocar system can include first inserting a valve having a valve body into the valve housing. A compression ring, for example, coated with an ultraviolet bonding agent, is then placed into the valve housing adjacent and abuttingly contacting the valve in a "stacked" fashion. Following this, the second valve is inserted into the valve housing adjacent and abuttingly contacting the compression ring, and a cap seal ring coated with an ultraviolet bonding agent is placed into the valve housing abuttingly contacting outer peripheries of the second valve. Both the compression ring and cap seal ring can be coated with an ultraviolet bonding agent, along with the outer peripheries thereof abuttingly contacting the inner peripheries of the valve housing. Once each of the components is in its place, the entire cap assembly is placed in a compression system, wherein each component is compressed to its desired depth into the valve housing. At that point, an ultraviolet light is exposed to the ultraviolet bonding agent to cure the materials. Upon the completion of the curing, the cap assembly is formed as one unit. Beneficially, the second valve can be readily removed and exchanged for a replacement.

When constructing a trocar system, the cap assembly is abuttingly and releasably connected to a cannula. The proximal end portion of the cannula body has at least one valve housing mating portion associated therewith, and the cap seal ring positioned in the valve housing also has at least one cannula body mating portion or flange associated therewith so that the cap assembly matingly attaches to the cannula body in a secured position and whereby movement of the cap assembly, e.g., rotation, by a hand of a user, releases, e.g., unsecures or unlocks, the respective mating portions for ready removal of the cap assembly by the user with the valve and second valve and so that specimens, e.g., tissue, can be readily removed from the cannula body without damage by the first and second valve. Advantageously, the extraction of large tissue samples and/or gauze packs can be accomplished without removing the cannula from the area where various endoscopic procedures take place.

BRIEF DESCRIPTION OF THE DRAWINGS

So that the manner in which the features and advantages of the invention, as well as others which will become apparent, may be understood in more detail, a more particular description of the invention briefly summarized above may be had by reference to the embodiments thereof which are illustrated in the appended drawings, which form a part of this specification. It is to be noted, however, that the drawings illustrate only various embodiments of the invention and are therefore not to be considered limiting of the invention's scope as it may include other effective embodiments as well.

FIG. 6 is a perspective view of a septum valve of a trocar system according to an embodiment of the present invention;

FIG. 7 is a top plan view of a septum valve of a trocar system according to an embodiment of the present invention;

FIG. 8 is a bottom plan view of a septum valve of a trocar system according to an embodiment of the present invention;

FIG. 9A is a sectional view of a septum valve of a trocar system taken along line 9A-9A of FIG. 7 according to an embodiment of the present invention;

FIG. 9B is an enlarged fragmentary sectional view of a septum valve of a trocar system according to an embodiment of the present invention;

FIG. 16 is a side elevational view of a trocar system according to an embodiment of the present invention;

FIG. 17 is a top plan view of a cap assembly of a trocar system according to an embodiment of the present invention;

FIG. 24 is a perspective view of a valve of a trocar system according to an embodiment of the present invention;

FIG. 25 is a magnified, cut-away surface view according to an embodiment of the present invention;

FIG. 26 is a cross-sectional, cut-away view taken along line 26-26 of the valve of FIG. 24 according to an embodiment of the present invention.

DETAILED DESCRIPTION OF THE INVENTION

The present invention will now be described more fully hereinafter with reference to the accompanying drawings, which illustrate embodiments of the invention. This invention may, however, be embodied in many different forms and should not be construed as limited to the illustrated embodiments set forth herein. Rather, these embodiments are provided so that this disclosure will be thorough and complete, and will fully convey the scope of the invention to those skilled in the art. Like numbers refer to like elements throughout, the prime or double prime notation, if used, indicates similar elements in alternative embodiments.

Figure 1:
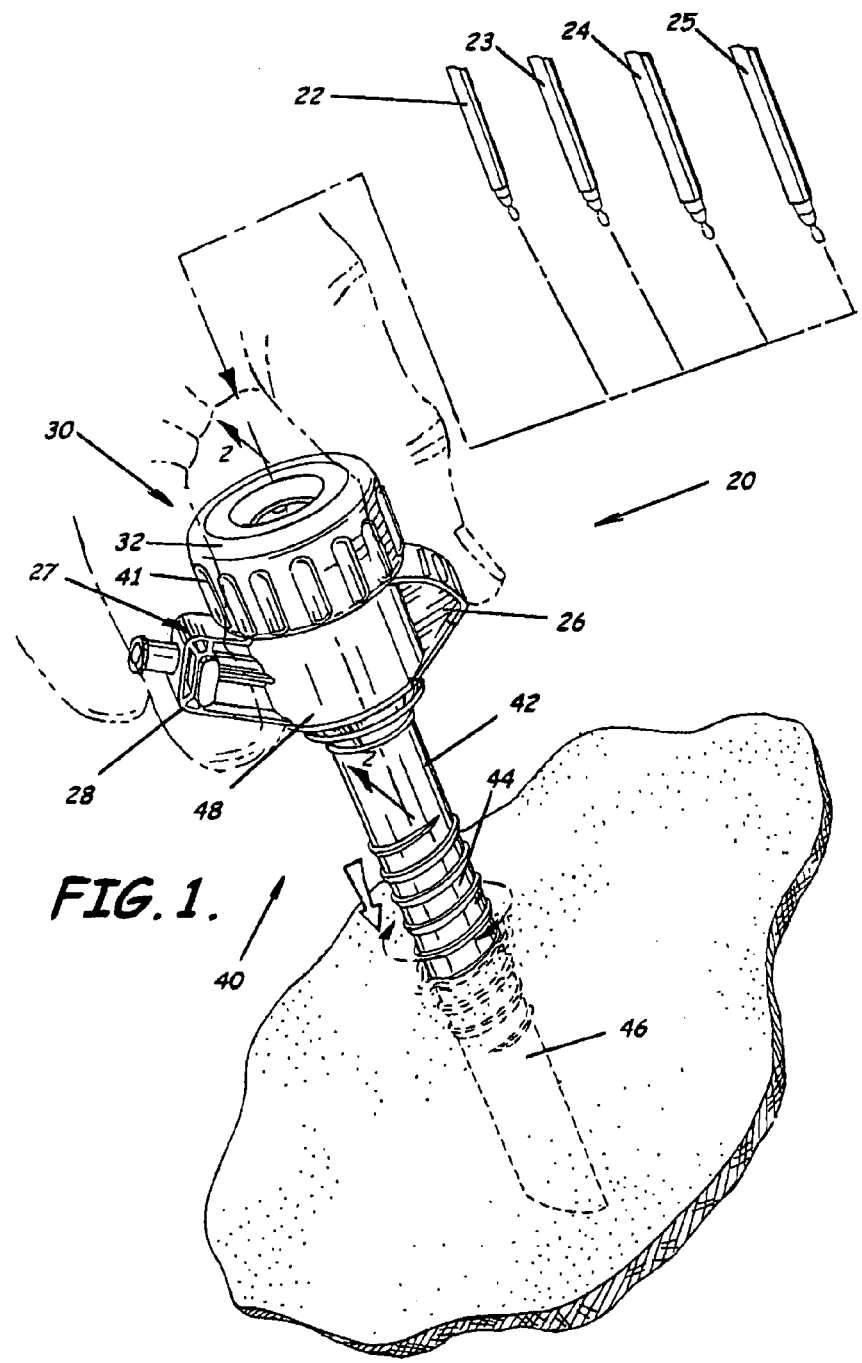
FIG. 1 is a perspective environmental view of a trocar system positioned within a layer of epidermis of a patient according to an embodiment of the present invention.

FIG. 1 illustrates a trocar system 20, which advantageously includes a cap assembly 30 having a valve housing 32. The valve housing 32 advantageously can have a roughened outer surface, e.g., a plurality of dimples 41, to enhance gripping and rotating thereof by a hand of a user. The trocar system 20 also includes a cannula 40 having an elongate cannula body 42. The cannula body 42 advantageously includes distal 46 and medial 44 portions thereof having a first diameter and a proximal portion 48 thereof connected to the medial portion 44 and having a second diameter. The second diameter can be advantageously larger or greater than the first diameter as illustrated. The finger gripping means 27 of the trocar system 20, for example, can be provided by a pair of finger grips 26, 28 connected to outer surfaces of the proximal portion 48 of the cannula body 42.

As illustrated in FIG. 1, the trocar system 20 further includes a plurality of tools 22, 23, 24, 25, each having an elongate body for extending through the cap assembly 30 and cannula 40. Advantageously, the plurality of tools 22, 23, 24, 25 each have a different diameter in the range of from about 5 millimeters to about 15 millimeters. The tools can be obturators or other endoscopic related tools for various endoscopic procedures.

Figure 2:
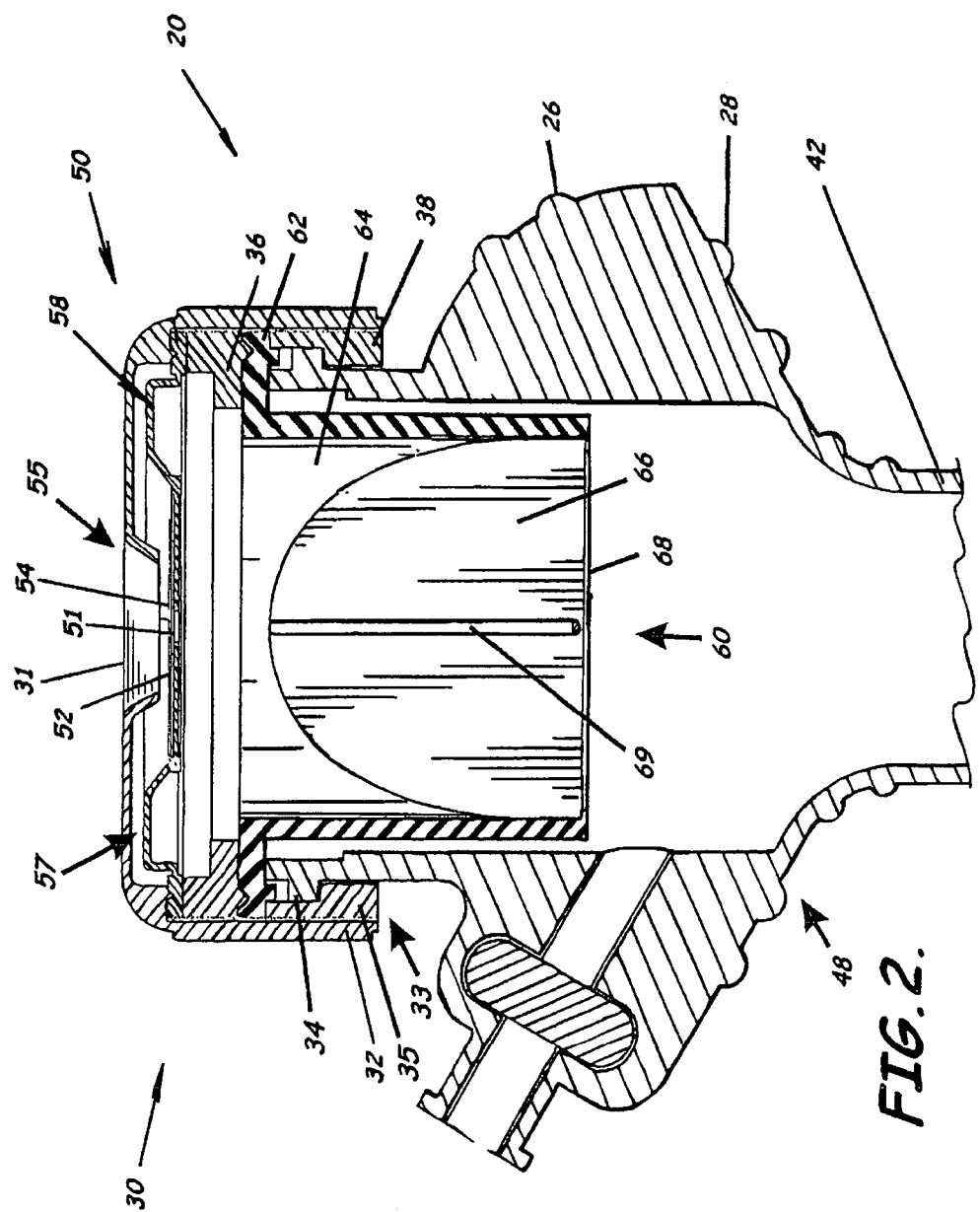
FIG. 2 is a fragmentary sectional view of a trocar system having first and second valves taken along line 2-2 of FIG. 1 according to an embodiment of the present invention.
Figures 3, 4:
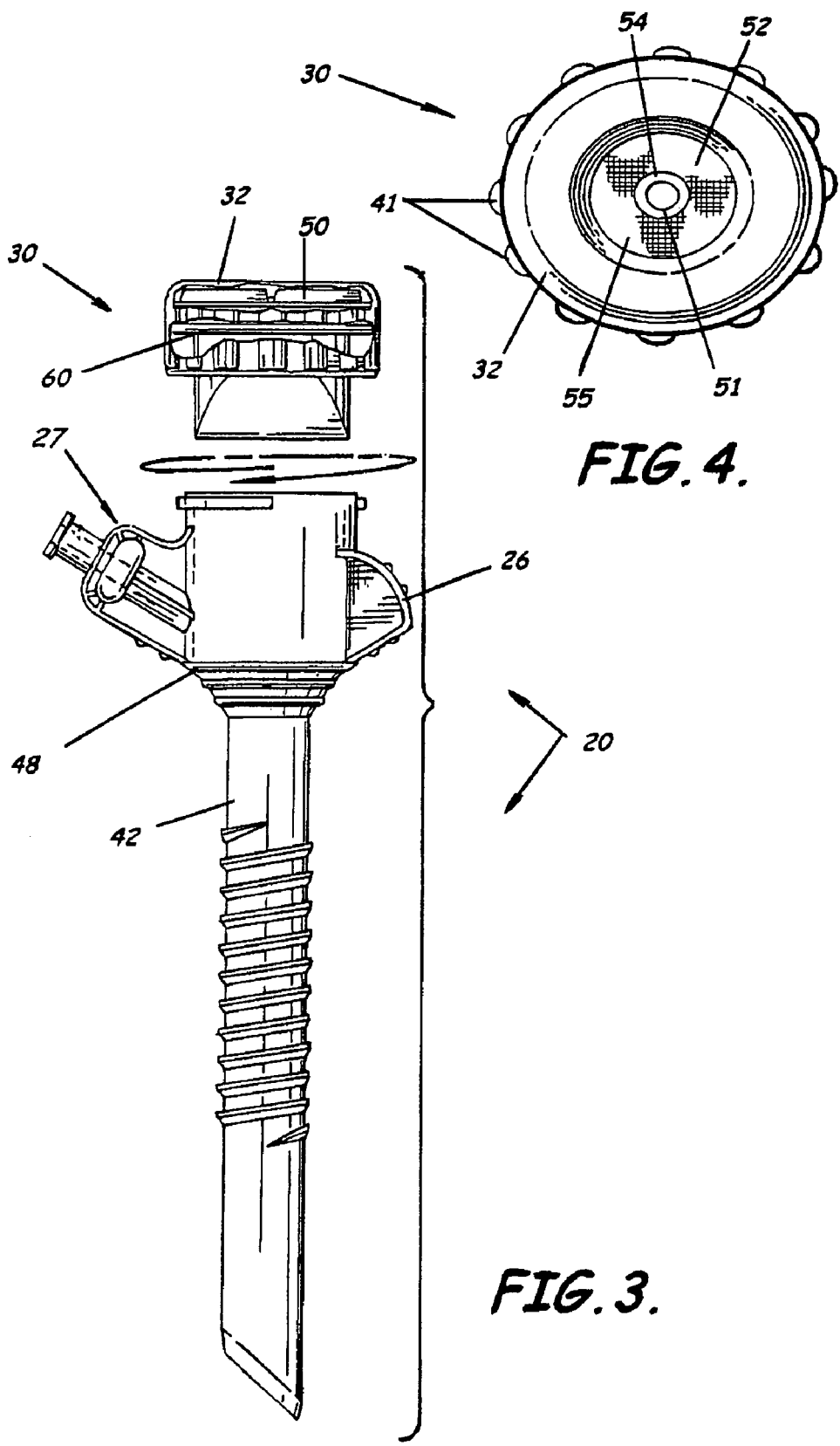
FIG. 3 is a side elevational view of a trocar system according to an embodiment of the present invention.
FIG. 4 is a top plan view of a cap assembly of a trocar system according to an embodiment of the present invention.

As perhaps best shown in FIGS. 1-9B, the cap assembly 30 according to an embodiment of the present invention, can include a valve housing 32 which has a substantially annular shape, a first opening 31 at a proximal end, and a second opening 33 at a distal end. The cap assembly 30 can also include a septum valve 50. The septum valve 50 is positioned adjacent the first opening 31 of the valve housing 32 and has an outer perimeter thereof fixedly connected to the valve housing 32. As perhaps best shown in FIG. 2, in an embodiment of the present invention, the portion of the cap assembly 30 forming the first opening 31 extends substantially axially downward toward the septum valve 50. An upper portion of first opening 31 is rounded so as not to have any right angle edges at the first opening 31, but resulting cross-section is a substantially cylindrical first opening 31 extending along the same axis as that for valve opening 51. As illustrated in FIGS. 2-3, the septum valve 50 is positioned entirely within the valve housing 32.

The septum valve 50 advantageously includes a valve body 55, which has an annular shaped valve opening 51 positioned in a medial portion of the valve body 55. The valve opening 51 is adapted to individually and separately receive a plurality of different elongate tools, each having a different diameter, therethrough. With such design, when any one of the plurality of elongate tools is positioned in the cap assembly 30 through the valve opening 51, a septum seal is maintained between peripheries of the valve body 55 surrounding the valve opening 51 and abuttingly contacting outer peripheries of the any one of the plurality of elongate tools extending therethrough. Additionally, the valve body 55 advantageously has first 52 and second 53 layers of a fabric material and a layer of elastomeric material 54 positioned between and contacting each of the first 52 and second 53 layers of the fabric material.

The septum valve 50 also advantageously includes a periphery valve section 57. The periphery valve section 57 is connected to and extends radially outwardly from peripheries of the valve body 55. The periphery valve section 57 has an outer perimeter thereof, defining the outer perimeter of the septum valve 50, which is fixedly connected to the valve housing 32. Additionally, the periphery valve section 57 has a plurality of rib members 59 radially extending substantially an entire distance between an outer perimeter of the valve body 55 and the outer perimeter of the periphery valve section 57. Advantageously, the rib members 59 are symmetrically positioned spaced-apart from each other. Still additionally, the periphery valve section 57 further has a plurality of convolutes 58, each positioned between and connected to any two adjacent rib members 59. The plurality of convolutes 58 are in a selected biased position before and after each of the plurality of different elongate tools extends through the valve opening 51 individually and separately. The plurality of convolutes 58 extend toward the proximal end of the valve housing 32 when in their biased position.

As illustrated in FIGS. 2-3, the cap assembly 30 also includes a second valve 60. The second valve 60 is advantageously positioned spaced-apart from the septum valve 50 and adjacent the second opening 33 of the valve housing 32. The second valve 60 advantageously has an annular flange portion 62 for enhancing the positioning of the second valve 60 within the valve housing 32, annular-shaped sidewalls 64 connected to the annular flange 62 and extending distally when positioned in the valve housing 32, and at least a pair of valve flaps 66 connected to and extending inwardly from the sidewalls 64 and flange portion 62. The sidewalls 64, for example, can extend distally of the end housing so that the flange portion 62 retains only portions of the valve 60 within the end housing 32 and yet slidably or in a spaced-apart relation have other portions which are positioned within the proximal portion 48 of the cannula body 42. The pair of valve flaps 66 has at least one slit 68 along common peripheral edges thereof through which the plurality of tools extend individually and separately. The second valve 60 also advantageously has ribs or rib members 67, e.g., formed integrally therewith as a single piece, and connected to the sidewalls 64, as illustrated, to reduce drag as will be understood by those skilled in the art. The second valve 60 can also be advantageously impregnated with a lubricant such as an oil material to enhance performance of the valve.

For the septum valve 50, the periphery valve section 57 is a continuous extension of the elastomeric layer 54 of the valve body 55. The periphery valve section 57 as constructed has a greater flexibility than the valve body 55. The elastomeric material advantageously includes polyisoprene or a fibrous material being impregnated with a silicon material to enhance the strength of the valve 50 and to enhance sliding and sealing of the plurality of tools. The fabric material advantageously includes a family of high-strength and resilient synthetic polymers containing polyurethane. One example of the fabric materials that can be used for constructing the septum valve is Spandex. For Spandex, there are three possible weaves to the fabric, which essentially incorporates Nylon and Lycra in an equally balanced bi-directional weave. The combination of elastomeric and fabric materials provides an enhanced recovery memory and resiliency. As constructed, the septum valve 50 advantageously has a stretching or elastic range to readily accommodate, e.g., auto-reduction, tools or other instruments having a diameter of about 5 millimeters to about 15 millimeters as understood by those skilled in the art, while still maintaining pneumoperitoneum. The valve opening 51 of the valve body 55 has a diameter less than the diameter of each of the plurality of tools that extends through the septum valve 50 so that a secured septum seal is provided around outer peripheries of each of the plurality of tools. The second valve 60 advantageously has this range as well, but individually can even have a greater range, e.g., 1 millimeter to 13 or 14 millimeters. Accordingly, with the septum valve 50 and second valve 60 in combination, the trocar system advantageously can receive different diameter instruments without the necessity of switching cannulas or valve systems.

The septum valve can advantageously have various embodiments. As illustrated in FIGS. 6-9B and 11-13, wiper region, which is the medial region of the valve body surrounding the peripheries of the valve opening and is formed of the elastomeric material, can have different thicknesses. In one embodiment, the wiper region has a much greater or larger thickness than the adjacent fabric region, as illustrated in FIGS. 6-9B. That is, the fabric layers 52, 53 have much greater or larger peripheries adjacent the valve opening 51 than the periphery of the elastomeric layer 54 surrounding the valve opening 51. In alternative embodiments, the wiper region is getting narrower and the thickness of the wiper is getting closer to the thickness of the adjacent fabric region.

Figure 5:
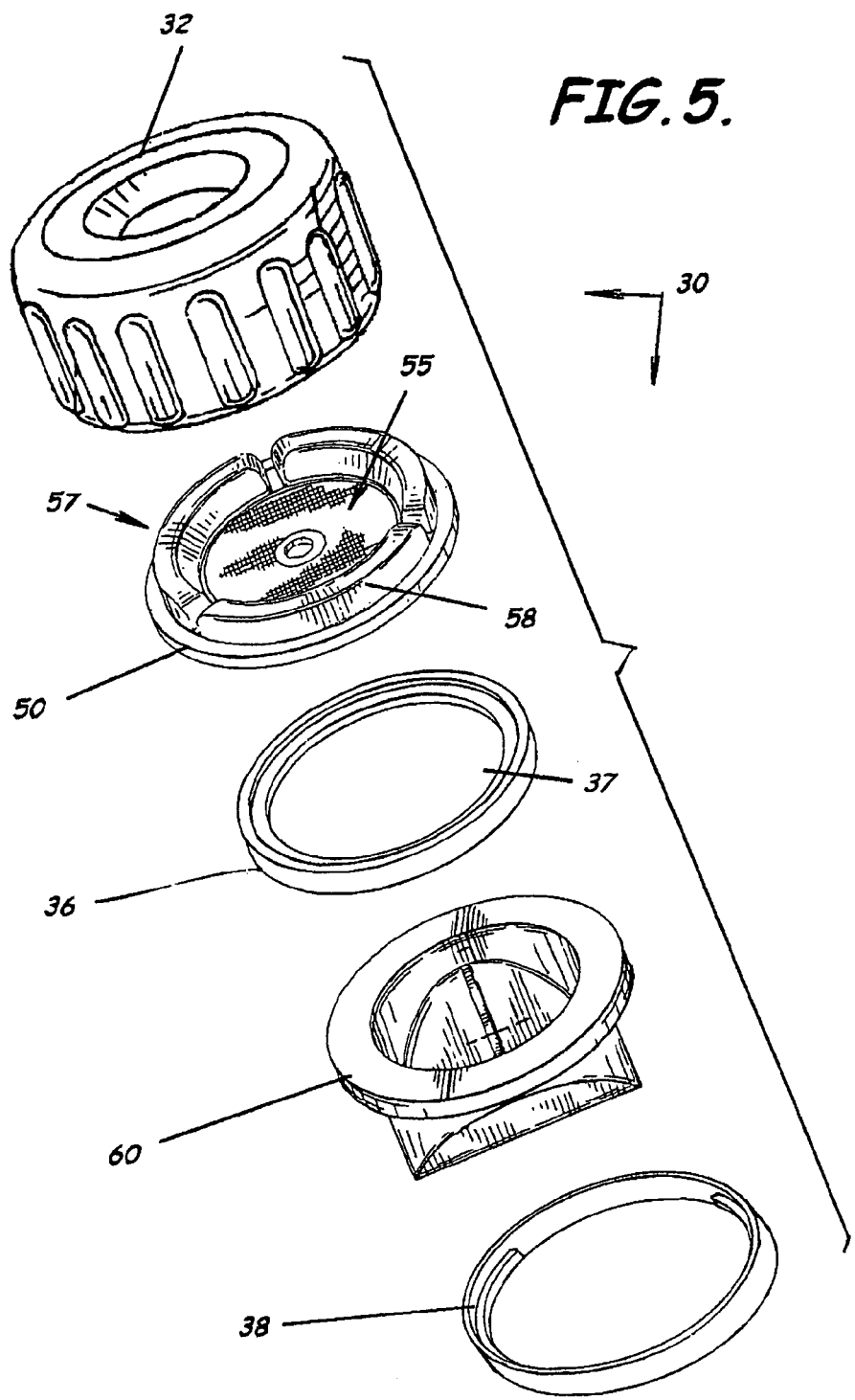
FIG. 5 is an exploded view of a cap assembly of a trocar system according to an embodiment of the present invention.
Figure 10:
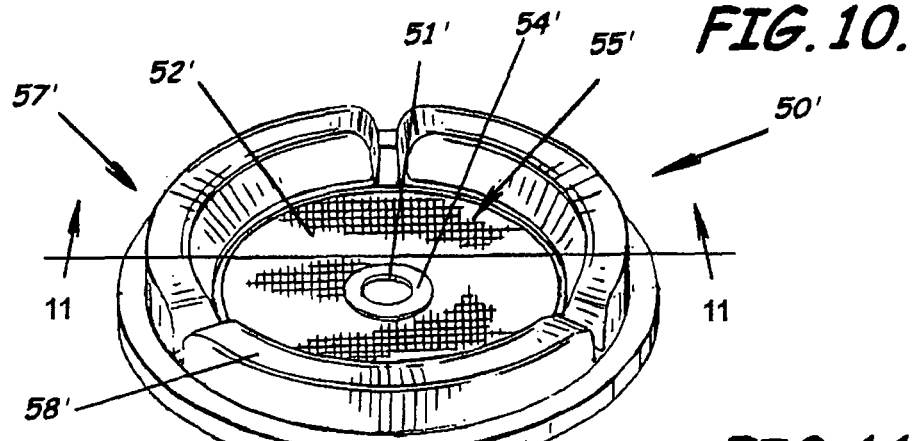
FIG. 10 is a perspective view of an alternate embodiment of a septum valve of a trocar system according to an embodiment of the present invention.
Figure 11:
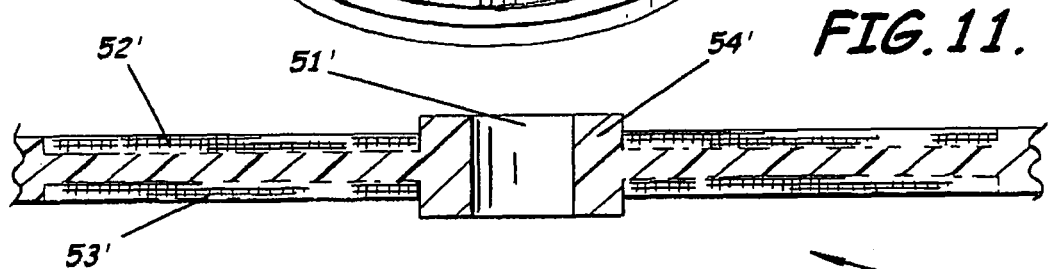
FIG. 11 is an enlarged fragmentary sectional view of an alternate embodiment of a septum valve of a trocar system taken along line 11-11 of FIG. 10 according to an embodiment of the present invention.
Figure 12:
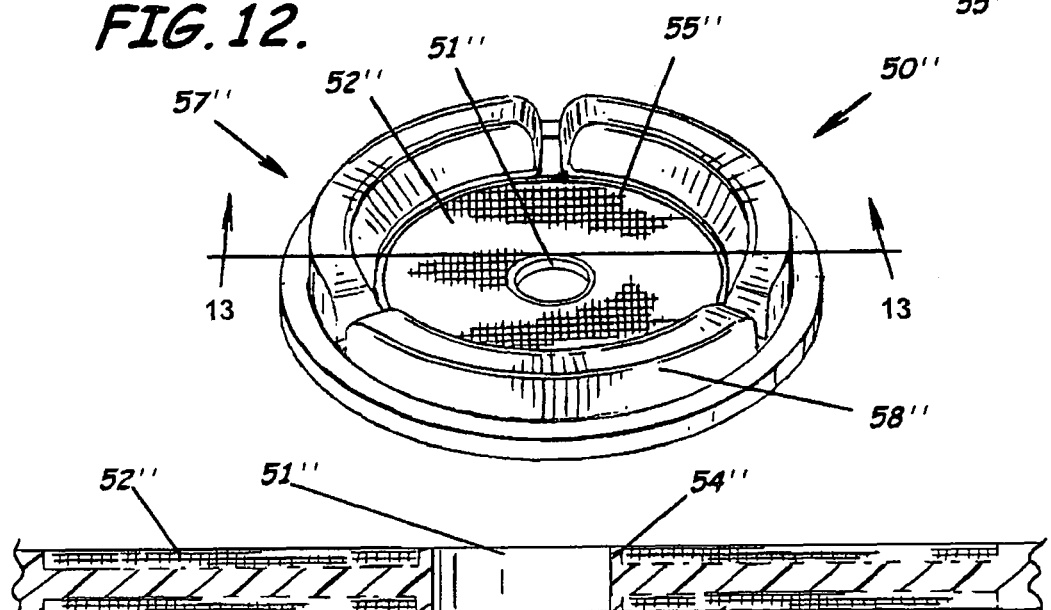
FIG. 12 is a perspective view of an alternate embodiment of a septum valve of a trocar system according to an embodiment of the present invention.
Figure 13:
FIG. 13 is an enlarged fragmentary sectional view of an alternate embodiment of a septum valve of a trocar system taken along line 13-13 of FIG. 12 according to an embodiment of the present invention.

Notably, the septum valve 50 is advantageously fixedly secured to the valve housing 32. FIG. 5 illustrates a construction process of the cap assembly 30. To provide secure sealing, the septum valve 50 having the valve body 55 and periphery valve section 57 is first inserted into the valve housing 32 with the convolutes 58 extending towards the proximal end of the valve housing 32. Then a compression ring 36 coated with an ultraviolet bonding agent is placed into the valve housing 32 adjacent and abuttingly contacting the septum valve 50 in a "stacked" fashion. Following this, the second valve 60 is inserted into the valve housing 32 adjacent and abuttingly contacting the compression ring 36, and a cap seal ring 38 coated with an ultraviolet bonding agent is placed into the valve housing 32 abuttingly contacting outer peripheries of the second valve 60. Both the compression ring 36 and cap seal ring 38 are advantageously coated with an ultraviolet bonding agent along the outer peripheries thereof abuttingly contacting the inner peripheries of the valve housing 32. The compression ring 36 also advantageously extends radially inward axially below the valve body 55 and forms a compression ring opening 37 substantially in-line with the valve opening 51 and the first opening.

Once each of the components is in its place, the entire cap assembly is placed in a compression system, wherein each component is compressed to its desired depth into the valve housing. At that point, an ultraviolet light is exposed to the ultraviolet bonding agent to cure the materials. The curing takes place in about 8 seconds. Upon the completion of the curing, the cap assembly 30 is formed as one unit.

When constructing a trocar system according to an embodiment of the present invention, the cap assembly 30 is abuttingly connected to the cannula 40. The proximal end portion 48 of the cannula body 42 has at least one valve housing mating portion 34 associated therewith and the valve housing 32 also has at least one cannula body mating portion 35 associated therewith so that the cap assembly 30 matingly attaches to the cannula body 42 in a secured position, and whereby movement of the cap assembly 30, e.g., rotational, by a hand of a user releases, e.g., unsecures or unlocks, the respective mating portions 34, 35 for ready removal of the cap assembly 30 by the user with the septum valve 50 and second valve 60 positioned therein and so that specimens, e.g., tissue, can be readily removed from the cannula body 42 without damage by the septum valve 50 and second valve 60. The extraction of large tissue samples and/or gauze packs can be accomplished without removing the cannula from the area where various endoscopic procedures take place.

The cannula body 42 can be advantageously formed of a clear plastic material so that direct visualization of specimen removal and instrument passage can be advantageously provided. This, for example, allows various types of cutting, gripping, or other types of tools to be inserted through the cannula 40 for various endoscopic procedures. As illustrated in FIGS. 1-13 and as described 11 above, the present invention also includes embodiments of a method of using a trocar system 20 including the steps of providing a cap assembly 30, which includes a septum valve 50, 50', 50" and inserting a tool 22, 23, 24, 25 through the septum valve 50, 50', 50" and cap assembly 30. During the insertion, the convolutes 58, 58', 58" of the periphery valve section 57, 57', 57" flex inwardly around the medial portion of the valve body 55, 55', 55" and consequently, the periphery valve section 57, 57', 57" is deformed temporarily so that the valve body 55, 55', 55" extends distally by contact pressure from the tool 22, 23, 24, 25 and so that a distal end of the tool 22, 23, 24, 25 is guided toward the valve opening 51, 51', 51". The unique symmetric rib structure of the periphery valve section 57, 57', 57" reinforces the movement of the convolutes 58, 58', 58" and the recovery of the convolutes 58, 58', 58". Because the septum valve 50, 50', 50" is constructed in a thin and relatively flat profile, the septum valve 50, 50', 50" functions like a thin elastic membrane. The membrane flexes inwardly and outwardly around the medial portion of the valve body 55, 55', 55" with the outer peripheries fixedly secured within the valve housing 32 and does not float or rotate in the valve housing 32. Upon the complete insertion of the tool 22, 23, 24, 25, the convolutes 58, 58', 58" flex outwardly around the medial portion of the valve body 55, 55', 55" and consequently, the periphery valve section 57, 57', 57" is retracted to its selected biased position. This method also includes extending the tool 22, 23, 24, 25 through a cannula body 42 matingly connected to the cap assembly 30 at a proximal portion 48 thereof, detaching the cap assembly 30 from the cannula body 42 and removing tissue or other specimen, as understood by those skilled in the art, from the cannula body 42.

Embodiments of the septum valve 50, 50', 50" includes a valve body 55, 55', 55" having an annular-shaped valve opening 51, 51', 51" positioned in a medial portion of the valve body 55, 55', 55" and adapted to receive a plurality of tools 22, 23, 24, 25 individually and separately therethrough. The valve body 55, 55', 55" advantageously has first 52, 52', 52" and second 53, 53', 53" layers of a fabric material and a layer of elastomeric material 54, 54', 54", 54''' positioned between and contacting each of the first and second layers of the fabric material. The septum valve 50, 50', 50" also includes a periphery valve section 57, 57', 57" connected to and extending radially outwardly from peripheries of the valve body 55, 55', 55" and having an outer perimeter thereof. The periphery valve section 57, 57', 57" advantageously has a plurality of rib members 59, each radially extending substantially an entire distance between an outer perimeter of the valve body 55, 55', 55" and the outer perimeter of the periphery valve section 57, 57', 57" and symmetrically positioned spaced-apart from each other (see FIGS. 2, 6-9B, 11-13). The periphery valve section 57, 57', 57" advantageously has a greater flexibility than the valve body 55, 55', 55".

Because embodiments of a septum valve 50, 50', 50", according to the present invention, have a relatively flat and thin profile and because peripheries of a septum valve 50, 50', 50" are fixedly connected to a valve housing 32, the septum valve 50, 50', 50" advantageously can operate like a fixed membrane that flexes distally toward the cannula 40 to allow tools 22, 23, 24, 25 used with the valve 50, 50', 50" to be guided toward and readily inserted into the valve opening 51, 51', 51". Yet, because tools 22, 23, 24, 25 can be sharp or point on distal ends thereof, the fabric or reinforced layers protect the membrane operation from tears or punctures during insertion of a tool 22, 23, 24, 25. Further, because various types and diameters of tools can be used by medical personnel, embodiments of a septum valve advantageously allow one type of valve, cannula, or trocar system to be readily used for all of these various sizes and types of tools.

As shown in FIGS. 14-23, embodiments of the present invention employ a nonplanar valve 150 which can be used with the cannula 40. Note, for simplicity, components common to both the embodiments described with reference to FIGS. 1-9B, such as the cannula 40, and the embodiments that will be described will retain their original numbering. Those components not common will be renumbered accordingly.

Figure 14:
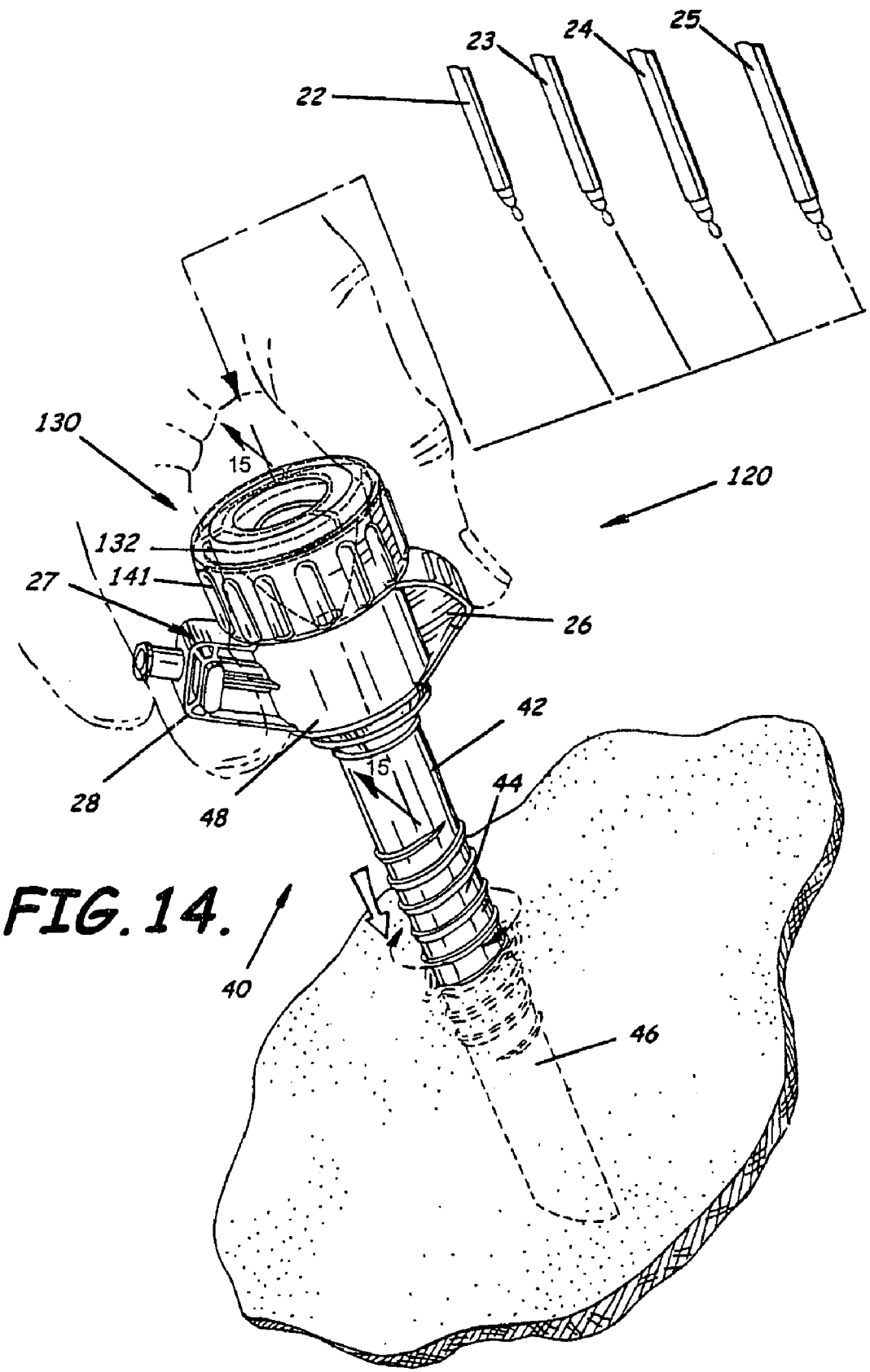
FIG. 14 is a perspective environmental view of a trocar system positioned within a layer of epidermis of a patient according to an embodiment of the present invention.
Figure 15:
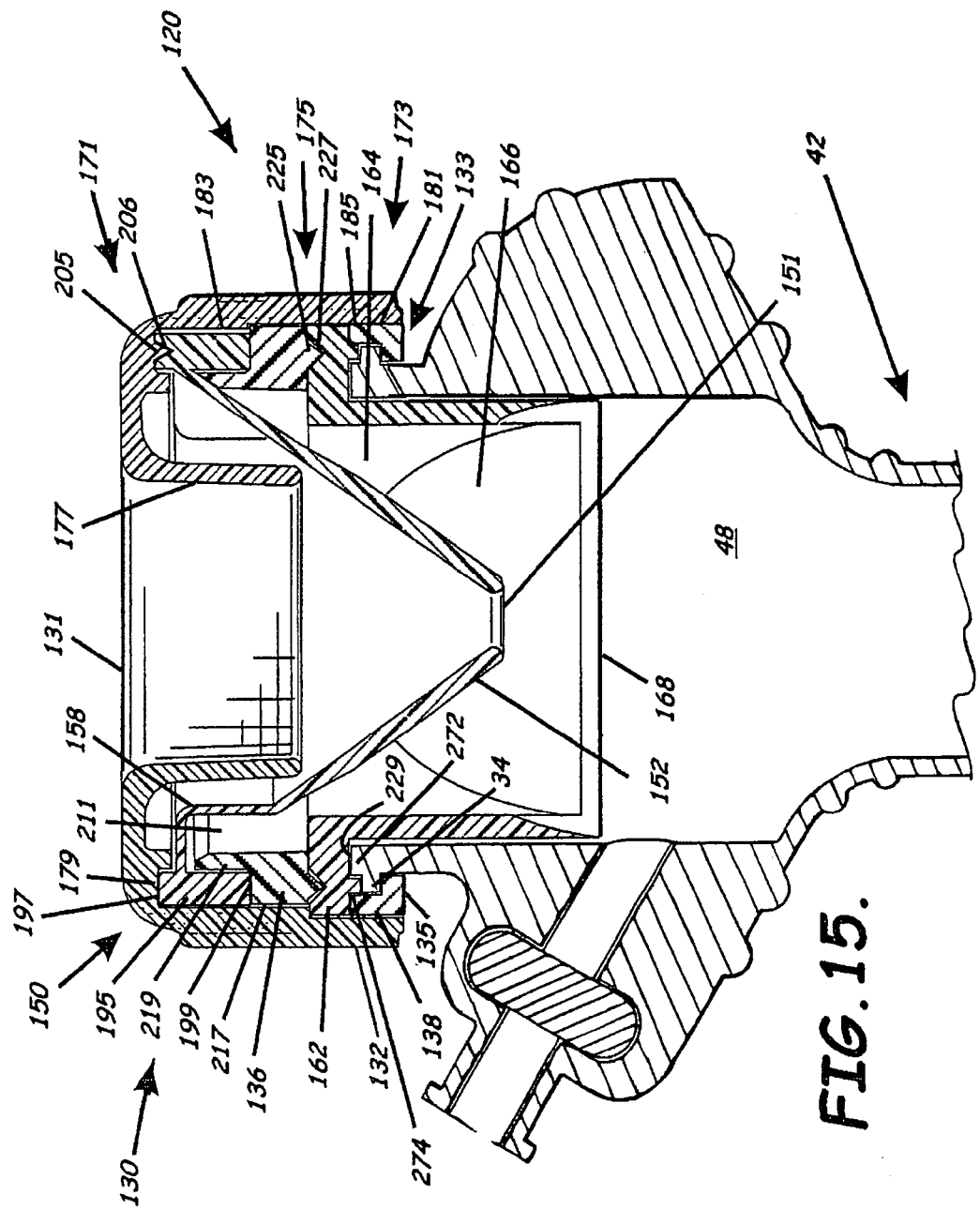
FIG. 15 is a fragmentary sectional view of a trocar system having first and second valves taken along line 15-15 of FIG. 14 according to an embodiment of the present invention.
Figure 18:
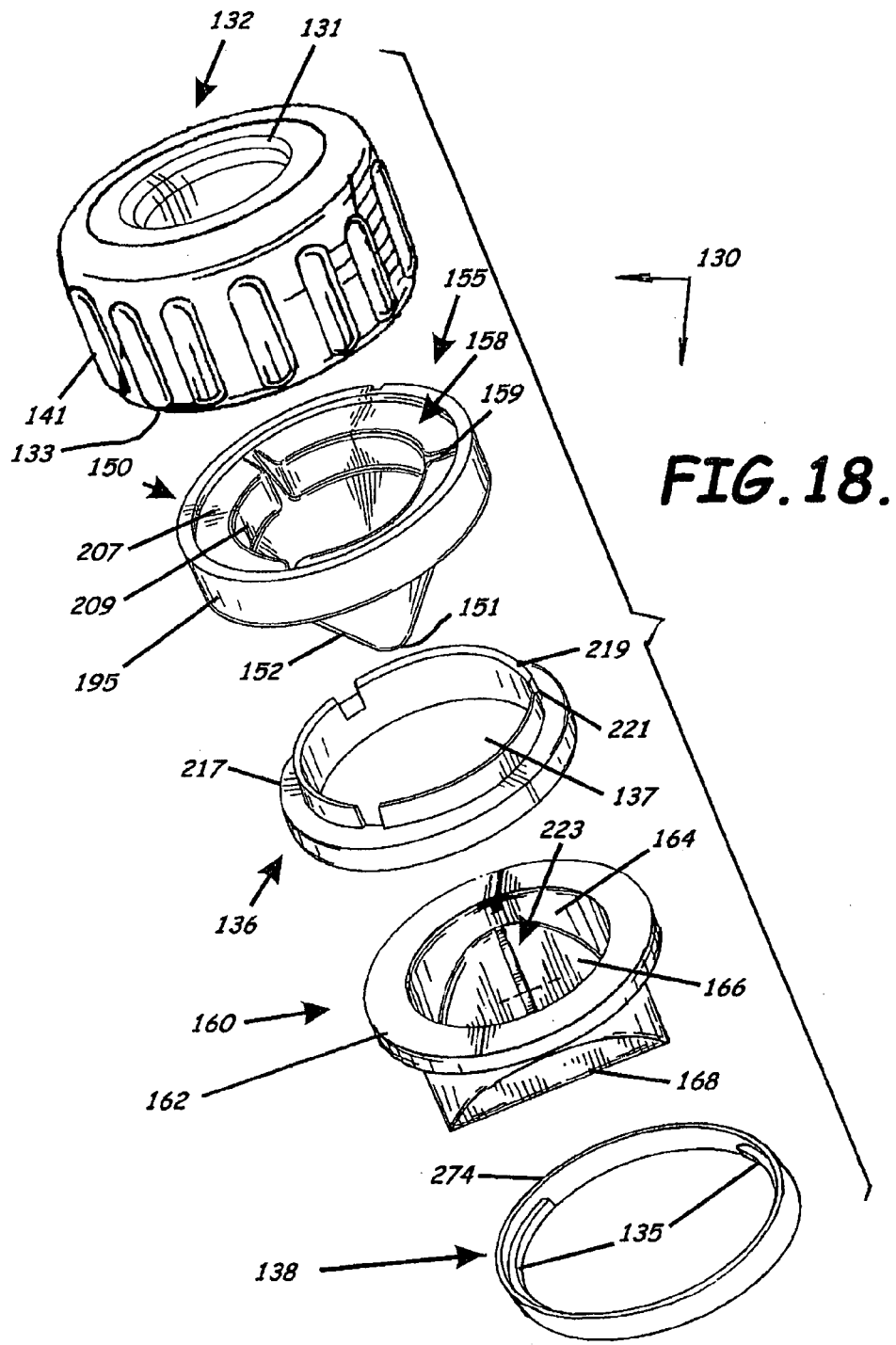
FIG. 18 is an exploded view of a cap assembly of a trocar system according to an embodiment of the present invention.
Figure 19:
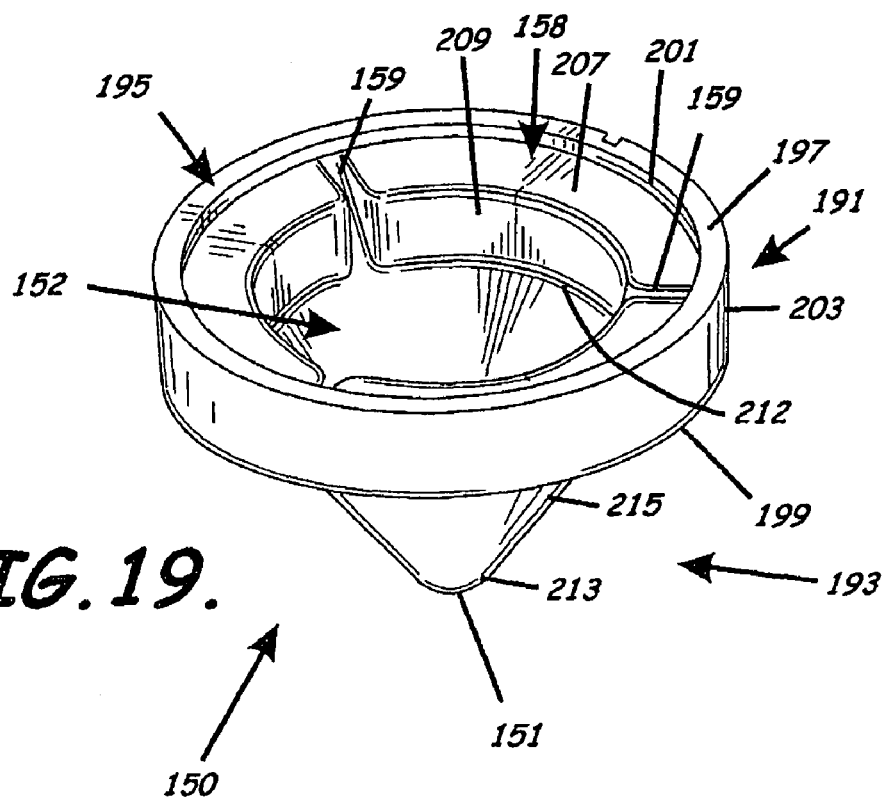
FIG. 19 is a perspective view of a valve of a trocar system according to an embodiment of the present invention.
Figure 20:
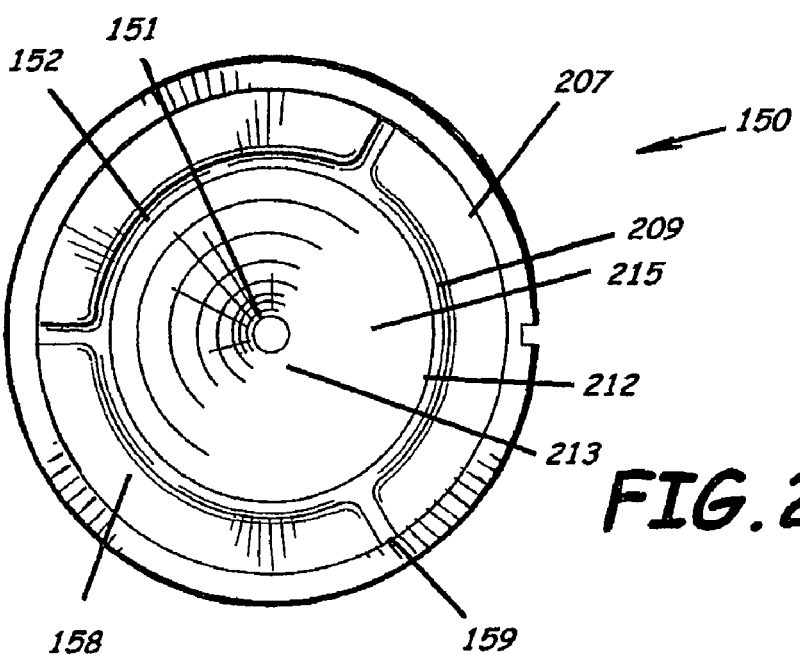
FIG. 20 is a top plan view of a valve of a trocar system according to an embodiment of the present invention.
Figure 21:
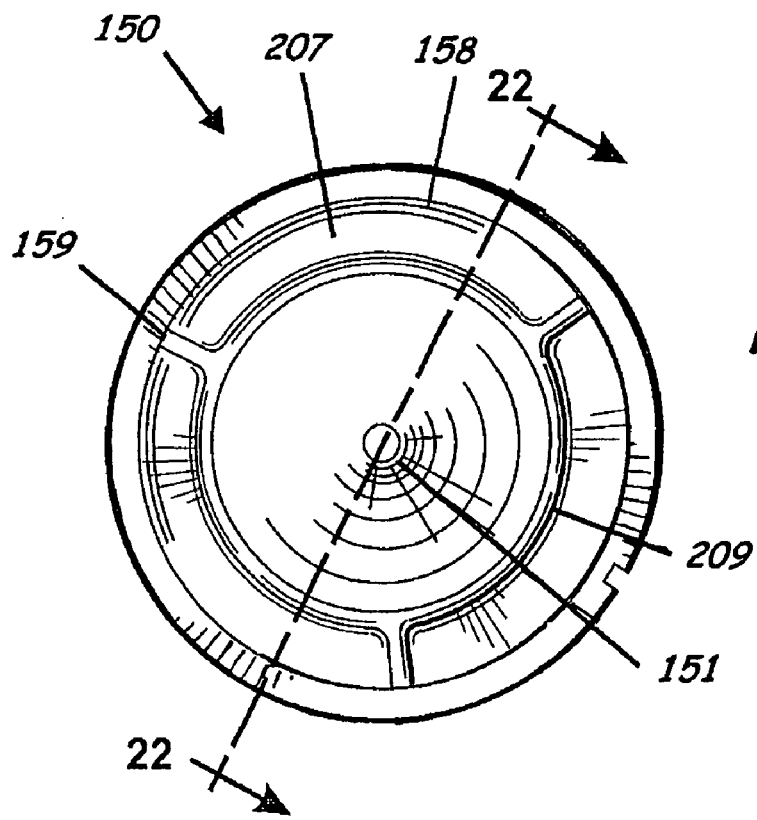
FIG. 21 is a bottom plan view of a valve of a trocar system according to an embodiment of the present invention.
Figure 22:
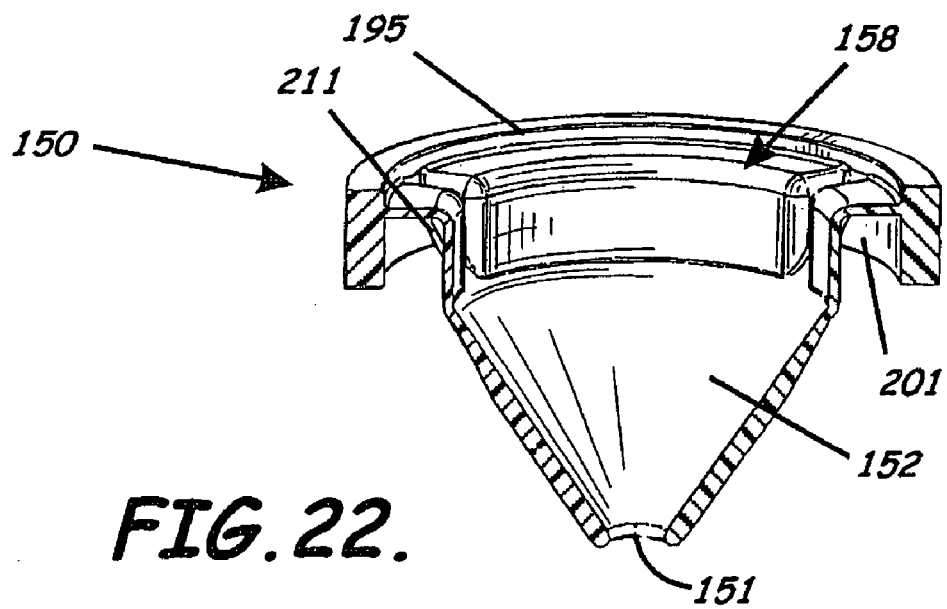
FIG. 22 is a sectional view of a valve of a trocar system taken along line 22-22 of FIG. 21 according to an embodiment of the present invention.

As perhaps best shown in FIGS. 14, 15, and 18, according to an embodiment of the present invention, a cap assembly 130 of a trocar system 120 includes a valve housing 132. The valve housing 132 which can have, for example, a substantially annular shape, can include a proximal end housing portion 171, a distal end housing portion 173, and a medial housing portion 175 connected to and extending therebetween. The proximal end housing portion 171 can include a first opening 131 having a first opening diameter defined by portions of an inner valve housing sidewall 177 extending distally in a substantially axial direction. The inner valve housing sidewall 177 forming the first opening 131 extends substantially axially downward toward a valve opening 151 of a valve 150, described below. The upper portion of the first opening 131 can be rounded so as not to have any right angle edges at the first opening 131, but with the resulting cross-section forming a substantially cylindrical first opening 131 extending along the same axis as that for the valve opening 151. The proximal end housing portion 171 can also include an annular valve ring recess 179 for retaining the valve 150. The distal end housing portion 173 can include a second opening 133 having a second opening diameter defined by a distal valve housing sidewall 181 extending in a substantially axial direction. The medial housing portion 175 can includes a first proximal valve housing inner perimeter surface 183 and a second distal valve housing inner perimeter surface 185 which can have a perimeter size or circumference the same or slightly larger than that of the first proximal valve housing inner perimeter surface 183.

As perhaps best shown in FIGS. 15 and 18-22, the valve 150 can include a valve body 155 positioned at least partially within the valve housing 132, axially aligned with the first opening 131 of the valve housing 132. As perhaps best shown in FIG. 19, the valve body includes a proximal valve section 191 fixedly positioned entirely within the valve housing 132 (see FIG. 15) and a distal valve section 193 extending axially from the proximal valve section 191. The proximal valve section 191 includes a valve ring 195 positioned in the valve ring recess 179 (FIG. 15) of the valve housing 132. The valve ring 195 has a proximal surface 197, a distal surface 199, an inner perimeter surface 201, and an outer perimeter surface 203 defining an outer perimeter of the valve body 155. The proximal valve section 191 also can include a plurality of convolutes 158, each having a first sidewall 207 extending radially inwardly from a portion of the inner perimeter surface 201 of the valve ring 195 and a second sidewall 209 extending axially from the first sidewall 207, substantially parallel to or slightly angled from the inner perimeter surface 201 of the valve ring 195, and forming an inner radial periphery of the proximal valve section 191. The inner perimeter surface 201 of the valve ring 195, the first sidewall 207, and the second sidewall 209 of each of the plurality of convolutes 158 form a respective convolute recess 211. The proximal valve section 191 can also include a plurality of rib members 159 (see, e.g., FIGS. 18 and 20) each radially extending substantially an entire distance between the inner radial periphery of the proximal valve section 191 and inner perimeter surface 201 of the valve ring 195 and symmetrically positioned spaced-apart from each other.

The distal valve section 193 can extend axially from the proximal valve section 191 and can include a valve extension 152 extending axially from the plurality of convolutes 158. The valve extension 152 can have a proximal end portion 212 substantially connected to a distal portion of each of the plurality of convolutes 158, a distal end portion 213, and a medial portion 215 connected to and extending therebetween. According to an embodiment of the valve extension 152, the medial portion 215 can have a substantially frusto-conical or other similar conical-form shape, as illustrated. The distal valve section 193 includes a valve opening 151 positioned in the distal end portion 213 of the valve extension 152, which can have, for example, an annular shape. The valve opening 151 is adapted to individually and separately receive therethrough any one of the plurality of different elongate tools 22, 23, 24, 25, each having a different diameter so that when any one of the plurality of elongate tools is positioned through the valve opening 151, a septum-type seal is maintained between peripheries of the distal end portion 213 of the valve extension 152 surrounding the valve opening 151 and outer peripheries of any one of the plurality of elongate tools when extending therethrough. As noted previously, the plurality of tools 22, 23, 24, 25, (FIGS. 1 and 14) each have an elongate body for extending through the valve housing 132, the valve opening 151 of the valve 150, and the cannula 40.

The plurality of convolutes 158 are each positioned between and connected to any two adjacent rib members 159. According to an embodiment of the convolutes 158, each convolute 158 can be in a selected biased position before and after each of the plurality of different elongate tools, individually and separately, extends through the valve opening 151. According to an embodiment of the present invention, the combination of the convolutes 158 and the valve extension 152 allow for axial movement of the tools 22, 23, 24, 25, without a corresponding movement within the valve opening 151 with respect to outer peripheries of the tools.

The valve body 155, in general, and the portion of the valve extension 152 surrounding the opening 151, in particular, can be formed of a flexible material to provide the elastic range necessary to accommodate the plurality of elongate tools 22, 23, 24, 25. According to an embodiment of the valve body 155, the flexible material advantageously can include a silicon material coated with paralene, available through various manufacturers, including Dow Corning Corp., to enhance the strength of the valve 150 and to enhance sliding and sealing of the plurality of tools 22, 23, 24, 25.

As shown in FIGS. 15, 16, and 18, the cap assembly 130 can also include a compression ring 136 positioned in the valve housing 132 at a medially axial position between the first and second openings 131, 133, of the valve housing 132, abuttingly contacting an axially facing distal surface 199 of the valve ring 195. The compression ring 136 includes a compression ring opening 137, substantially aligned axially with the first opening 131 of the valve housing 132 to allow extension of the plurality of elongate tools therethrough. The compression ring opening 137 can also be sized to allow at least portions of the inner valve housing sidewall 177 and valve 150 to extend therethrough. The compression ring 136 also includes an outer perimeter surface 217 having a radial diameter sized so that the compression ring 136 substantially abuttingly contacts the proximal valve housing inner perimeter surface 183 when positioned within the valve housing 132 and includes an annular flange 219 extending into each one of the plurality of convolute recesses 211.

The compression ring 136 is positioned to compress the valve ring 195 against an axially facing inner surface and an axially facing shoulder of the proximal end housing portion 171 of the valve housing 132 which together, along with a portion of the first proximal valve housing inner perimeter surface 183 of the medial housing portion 175, form the valve ring recess 179 and/or compress the valve ring 195 against the first proximal valve housing inner perimeter surface 183 of the medial housing portion 175, to hold the valve ring 195 in the valve ring recess 179 to fixedly position the valve 150 within the valve housing 132. That is, the compression ring 136 is positioned so that the proximal valve housing inner perimeter surface 183, surfaces forming the valve ring recess 179, and an annular flange 219 of the compression ring 136 rigidly hold the valve ring 195 within the valve housing 132.

The annular flange 219 of the compression ring 136 can include a plurality of notches 221 symmetrically positioned spaced-apart from each other so that each of the notches 221 aligns with and receives a separate one of the plurality of rib members 159 to thereby rotationally align the compression ring 136 with the valve ring 195 when positioned in contact therewith. Alternatively, the annular flange 219 can include a plurality of separate spaced apart flanges (not shown) having a gap between each pair of flanges defining the notch 221 and aligned with the plurality of remembers 159 to thereby enhance positioning of the valve ring 195. To further enhance positioning of the valve ring 195, according to an embodiment of the valve housing 132 and valve ring 195, the axially facing inner surface of the proximal end housing portion 171 of the valve housing 132 can include one or more protuberances 205 extending at least partially along the length of the valve ring recess 179, and the proximal surface 197 of the valve ring 195 can include one or more recesses 206 or can deform to form a recess 206, as illustrated, to receive the one or more protuberances 205 to thereby enhance positioning of the valve ring 195 within the valve housing 132.

The cap assembly 130 can also include a second valve 160. The second valve 160 is advantageously positioned adjacent the second opening 133 of the valve housing 132, abuttingly contacting the compression ring 139. The second valve 160 advantageously has an annular flange portion 162 spaced axially from the valve ring of the first valve 150. The annular flange portion 162 can have a radial diameter sized so that the annular flange portion 162 substantially abuttingly contacts the distal valve inner housing perimeter surface 185 and an axially facing distal surface of the compression ring 136 adjacent the compression ring opening 137 to enhance the positioning of the second valve 160 within the valve housing 132. The second valve 160 includes a second valve opening 223 positioned within the annular flange portion 162 and, when positioned within the valve housing 132, is substantially aligned axially with the first and second openings 131, 133, of the valve housing 132 to allow extension of the plurality of elongate tools 22, 23, 24, 25, therethrough.

According to an embodiment of the present invention, annular-shaped sidewalls 164 are connected to the annular flange portion 162 and extend distally in a substantially axial direction when positioned in the valve housing 132. At least one pair of valve flaps 166 is connected to and extends inwardly from the sidewalls 164 and flange portion 162. The sidewalls 164, for example, can extend distally of the end of the valve housing 132 so that the flange portion 162 retains only portions of the valve 160 within the valve housing 132 and yet slidably or in a spaced-apart relation have other portions which are positioned within the proximal portion 48 of the cannula body 42. Similarly, portions of the valve extension 152 and/or the valve opening 151 of the first valve 150 can extend within the proximal portion 48 of the cannula body 42. The pair of valve flaps 166 has at least one opening or slit 168 along common peripheral edges thereof through which the tools 22, 23, 24, 25, can individually and separately extend. The second valve 160 also advantageously can have ribs or rib members (not shown), e.g., formed integrally therewith as a single piece, and connected to the sidewalls 164 to reduce drag as will be understood by those skilled in the art. The second valve 160 can also be advantageously impregnated with a lubricant such as an oil material to enhance performance of the valve. Note, according to an embodiment of the present invention, the illustrated sidewalls 164 can be replaced with other forms of extension extending from the annular flange portion 162 of the second valve 160. Further, the valve opening 168 can take other forms, such as an annular shaped opening or other known to those skilled in the art.

The second valve 160, in general, and the portion of the sidewalls 164 surrounding the opening 168, in particular, can be formed of a flexible material similar to that used in forming the first valve 150. For example, according to an embodiment of the second valve 160, the flexible material advantageously can include a silicon material coated in paralene to enhance the strength of the valve 160 and to enhance sliding and/or sealing of the plurality of tools 22, 23, 24, 25.

According to an embodiment of the cap assembly 130, in order to enhance positioning of the second valve 160, a proximal surface of the annular flange portion 162 of the second valve 160 can include an at least partially annular recess 227 or can deform to form a recess 227, as illustrated, to receive an at least partially annular protuberance 225 extending from a distal surface of the compression ring 136 to thereby enhance positioning of the second valve at least partially within the valve housing 132.

A distal surface of the annular flange portion 162 of the second valve 160 can further include a second valve annular-shaped recess 229 adapted to receive an axially extending annular-shaped flange 272 of the proximal portion 48 of the cannula 40 to thereby enhance positioning of at least part of the proximal portion 48 of the cannula 40 within the valve housing 132.

As shown in FIGS. 15, 16, and 18, the cap assembly 130 can also include a cap seal ring 138 positioned at least partially within the valve housing 132 and having an axially extending flange 274 positioned to abuttingly contact a distal surface of the annular flange portion 162 of the second valve 160 when positioned in the valve housing 132. The cap seal ring 138 can include a plurality of radially extending flanges 135 each adapted to engage outer peripheries of a separate one of the plurality of radially extending flanges 34 of the cannula 40 to slidably detachably connect the valve housing 132 to the cannula 40. The cannula 40 can also include an annular shaped axially extending flange adapted to engage the annular-shaped recess 229 of the second valve 160 to thereby enhance positioning of the cannula 40 securely against the second valve 160 when positioned in engagement with the radially extending flanges 135 of the cap seal ring 138.

Figure 23:
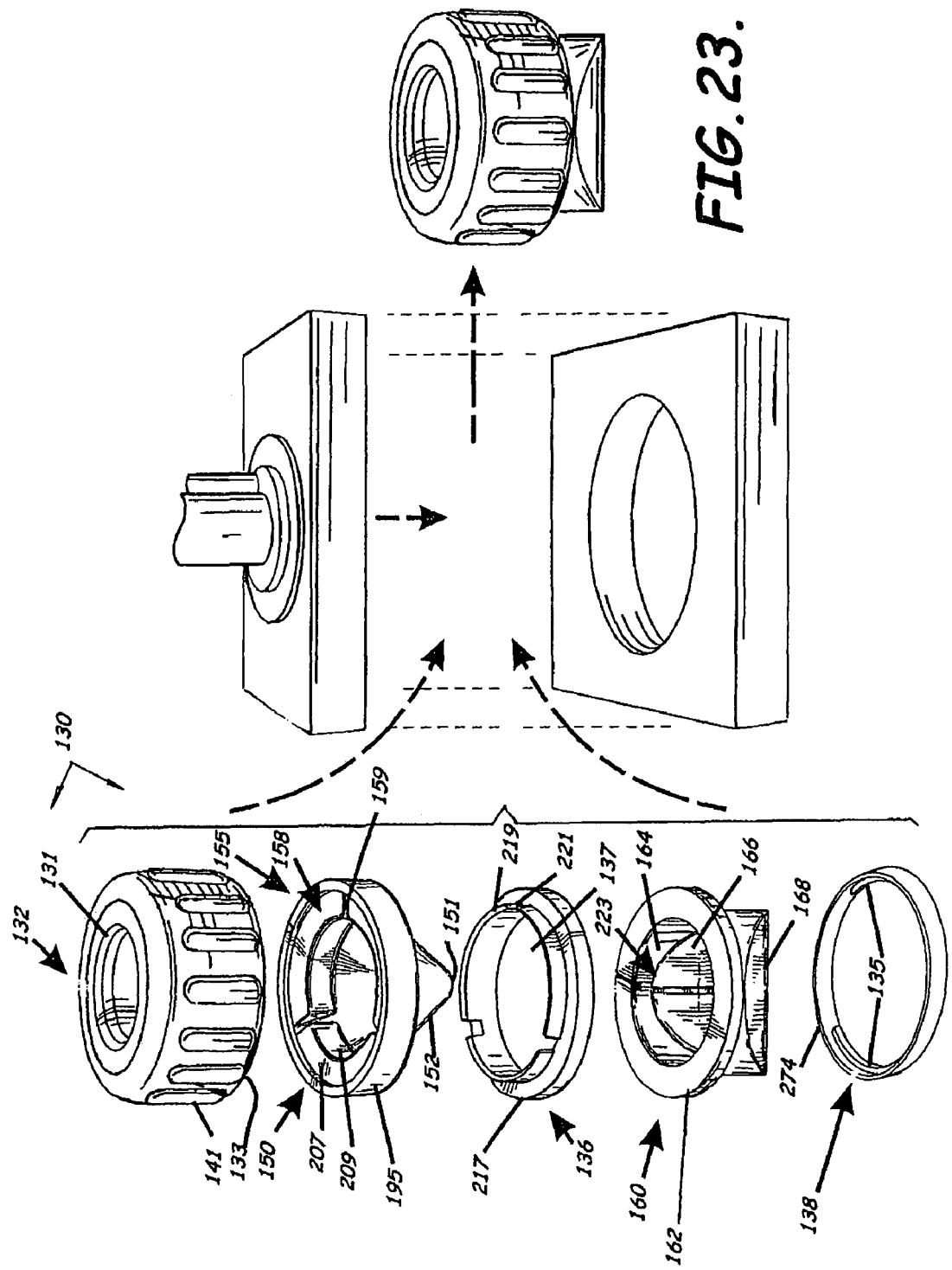
FIG. 23 is an environmental perspective view of a valve, valve mold, and a slab illustrating the formation of a valve according to an embodiment of the present invention.

As perhaps best shown in FIGS. 15, 18, and 23, embodiments of the present invention, a method of forming a trocar system 120, as constructed, for example, the valve 150 advantageously has a stretching or elastic range to readily accommodate, e.g., auto-reduction, tools or other instruments having a diameter of about 5 millimeters to about 15 millimeters as understood by those skilled in the art while still maintaining pneumoperitoneum. The valve opening 151 of the valve body 155 has a diameter less than the diameter of each of the tools 22, 23, 24, 25, that extend through the valve 150 so that a secured seal is provided around outer peripheries of each of the tools. The second valve 160 advantageously has this range as well, but individually can even have a greater range, e.g., 1 millimeter to 13 or 14 millimeters. Accordingly, with the valve 150 and second valve 160, in combination, the trocar system 120 advantageously can receive different diameter instruments without the necessity of switching cannulas or valve systems.

The valve 150 is advantageously fixedly secured to the valve housing 132. FIG. 23 illustrates an exemplary construction process of the cap assembly 130. To provide secure sealing, the valve 150 having the valve body 155 is first inserted into the valve housing 132. Then a compression ring 136, for example, coated with an ultraviolet bonding agent, is placed into the valve housing 132 adjacent and abuttingly contacting the valve 150 in a "stacked" fashion. Following this, the second valve 160 is inserted into the valve housing 132 adjacent and abuttingly contacting the compression ring 136, and a cap seal ring 138 coated with an ultraviolet bonding agent is placed into the valve housing 132 and abuttingly contacting outer peripheries of the second valve 160. Both the compression ring 136 and cap seal ring 138 can be coated with an ultraviolet bonding agent along the outer peripheries thereof abuttingly contacting the inner peripheries of the valve housing 132.

Once each of the components is in its place, the entire cap assembly is placed in a compression system, wherein each component is compressed to its desired depth into the valve housing 132. At that point, an ultraviolet light is exposed to the ultraviolet bonding agent to cure the materials. The curing takes place in about 8 seconds. Upon the completion of the curing, the cap assembly 130 is formed as one unit. Beneficially, the second valve 160 can be readily removed and exchanged for a replacement.

When constructing a trocar system 120, the cap assembly 130 is then abuttingly connected to the cannula 40. The proximal end portion 48 of the cannula body 42 has at least one valve housing mating portion 34 associated therewith and the cap seal ring 138 positioned in the valve housing 132 also has at least one cannula body mating portion or flange 135 associated therewith so that the cap assembly 130 matingly attaches to the cannula body 42 in a secured position and whereby movement of the cap assembly 130, e.g., rotation, by a hand of a user releases, e.g., unsecures or unlocks, the respective mating portions 34, 135 for ready removal of the cap assembly 130 by the user with the first and second valves 150, 160, and so that specimens, e.g., tissue, can be readily removed from the cannula body 42 without damage by the first and second valves 150, 160. The extraction of large tissue samples and/or gauze packs can be accomplished without removing the cannula 40 from the area where various endoscopic procedures take place.

As illustrated in FIGS. 14-22, embodiments of the present invention also include a method of using a trocar system 120 including the steps of providing a cap assembly 130, which includes a valve 150, as described above, and inserting a tool 22, 23, 24, 25 through the valve 150 and cap assembly 130. During the insertion, the convolutes 158 and the valve extension 152 flex so that the valve body 155 extends distally by contact pressure from the tool 22, 23, 24, 25 and so that a distal end of the tool 22, 23, 24, 25 is guided through the valve opening 151. The unique symmetric rib structure reinforces the movement of the convolutes 158 and the recovery of the convolutes 158 once the tool is extended through the valve opening 151. Because the valve 150 is constructed in a thin and relatively conical shaped profile, the valve 150 functions like a thin elastic membrane that flexes inwardly and outwardly along a fairly wide range of tool positions, without requiring the valve opening 151 to "slide" along the outer peripheries of the respective tool once positioned through the valve opening 151, and does not float or rotate in the valve housing 132. This method also includes extending the tool 22, 23, 24, 25 through a cannula body 42 matingly connected to the cap assembly 130 at a proximal portion 48 thereof. The method further includes the steps of detaching the cap assembly 130 from the cannula body 42 and removing tissue or other specimen as understood by those skilled in the art from the cannula body 42. Because various types and diameters of tools can be used by medical personnel, embodiments of a valve advantageously allow one type of valve, cannula, or trocar system to be readily used for all of these various sizes and types of tools.

As shown in FIGS. 24-26, embodiments of the present invention employ a nonplanar valve 150' which can also be used with the cannula 40. Note, for simplicity, components common to both the embodiments described with reference to FIGS. 1-23, such as the cannula 40, and the embodiments that will be described will retain their original numbering. Those components not common will be renumbered accordingly.

Similarly to valve 150, valve 150' can include a valve body 155' positioned at least partially within the valve housing 132, axially aligned with the first opening 131 of the valve housing 132, wherein distal valve section 193' extends axially from proximal valve section 191'. The proximal valve section 191' includes a valve ring 195. The proximal valve section 191' also can include a plurality of convolutes 158. The proximal valve section 191' can also include a plurality of rib members 159, each radially extending substantially an entire distance between the inner radial periphery of the proximal valve section 191' and inner perimeter surface 201 of the valve ring 195 and symmetrically positioned spaced-apart from each other.

The distal valve section 193' can extend axially from the proximal valve section 191' and can include a valve extension 152' extending axially from the plurality of convolutes 158. The valve extension 152' can have a proximal end portion 212 substantially connected to a distal portion of each of the plurality of convolutes 158, a distal end portion 213', and a medial portion 215' connected to and extending therebetween. According to an embodiment of the valve extension 152', the medial portion 215' can have a substantially frusto-conical or other similar conical-form shape, as illustrated. The distal valve section 193' includes a valve opening 151' positioned in the distal end portion 213' of the valve extension 152', which can have, for example, an annular shape. The valve opening 151' is adapted to individually and separately receive therethrough any one of the plurality of different elongate tools 22, 23, 24, 25, each having a different diameter so that when any one of the plurality of elongate tools is positioned through the valve opening 151', a septum-type seal is maintained between peripheries of the distal end portion 213' of the valve extension 152' surrounding the valve opening 151' and outer peripheries of any one of the plurality of elongate tools when extending therethrough. As noted previously, the plurality of tools 22, 23, 24, 25, (FIGS. 1 and 14) each have an elongate body for extending through the valve housing 132, the valve opening 151' of the valve 150', and the cannula 40.

The valve body 155', in general, and the portion of the valve extension 152' surrounding the opening 151', in particular, can be formed of a flexible material to provide the elastic range necessary to accommodate the plurality of elongate tools 22, 23, 24, 25. According to an embodiment of the valve body 155', the flexible material advantageously can include a silicon material coated with paralene, available through various manufacturers including Dow Corning Corp., to enhance the strength of the valve 150' and to enhance sliding and sealing of the plurality of tools 22, 23, 24, 25. Because ease of insertion and removal of the instruments is an important aspect during use of cannula 40, and because even small measures of improvement can translate into realized enhancement of performance, coatings and other measures directed toward improving lubricity can be advantageously supplemented, wherein a reduction in electrostatic adhesion between the valve 150' and the plurality of tools 22, 23, 24, 25 can serve to further enhance the ease of insertion and removal.

Figure 27:
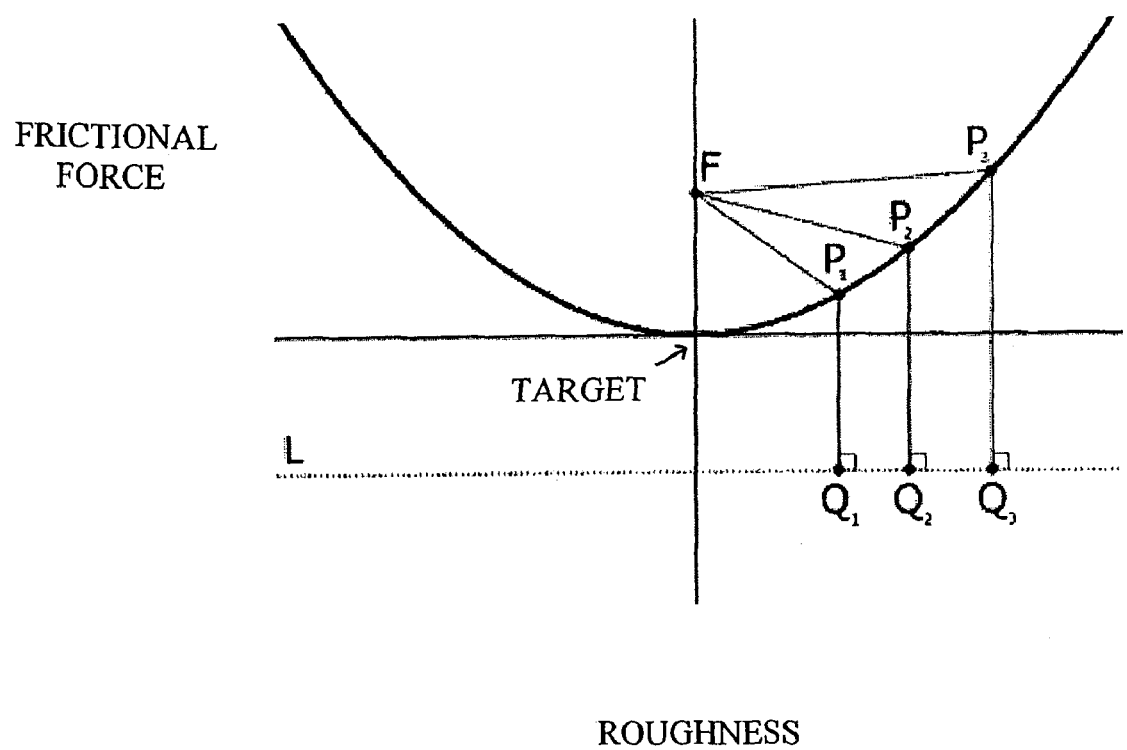
FIG. 27 is a graphical representation of the parabolic relationship between frictional force and roughness.

The relationship between frictional force and roughness is parabolic, as depicted in FIG. 27, wherein frictional forces are increased between both very smooth, as well as very rough surfaces, and wherein at the vertex of the parabola, a target roughness quality is represented that results in little or no frictional force. The smoothness of valve extension 152', therefore, can be specifically adjusted relative to previously described valve extension 152, wherein plurality of friction-reduction features 300 can be defined. That is, the valve body 155', in general, and the portion of the valve extension 152' proximate opening 151', in particular, can include plurality of friction-reduction features 300 to advantageously minimize electrostatic forces between instruments and the valve 150'. The plurality of friction-reduction features 300 is strategically configured to increase roughness of valve extension 152' in such a manner that movement toward the vertex along the demonstrated parabolic curve relating frictional force and roughness can be realized.

Preferably, the plurality of friction-reduction features 300 is comprised of plurality of protrusions 302, preferably defined on outer surface 304 and inner surface 306 of valve extension 152', preferably and generally over an area defined proximate and between medial portion 215' and distal end portion 213' of valve 150'. The friction-reduction features 300 are defined proximate the apical end of the valve 150' in anticipation of contact with the plurality of elongate tools 22, 23, 24, extended therethrough, and are further preferably defined on both opposing surfaces 304-306 in order that advantageous minimization of electrostatic forces may be realized also during contact between the valve body 155' and the second valve 160. In the preferred configuration, the plurality of protrusions 302 are tear-drop shaped, as shown, wherein this preferred shape functionally improves the manufacturing process, as well as serving to reduce the resistive forces between the contact surfaces of an inserted instrument and the valve 150' without compromise to the septum seal or to the inherent flexibility and adaptability of the valve 150', wherein a broad endoscopic instrument diameter range, from about 3 mm to 15 mm diameter, can be successfully accepted.

The preferred arrangement for the plurality of protrusions 302 may be generally described as six rows 308a-308f of tear-drop shaped knobs 310, wherein each row 308a-308f essentially encircles valve extension 152', as relative concentric circles. That is, the circumference of row 308a of tear-drop shaped knobs 310, as defined proximate valve opening 151', is slightly larger than the at-rest or non-expanded circumference of valve opening 151'. Similarly, the circumference of row 308b of tear-drop shaped knobs 310 is slightly larger than the circumference of row 308a, and so on, for the relationship of the circumference of row 308c relative to the circumference of row 308b, the relationship of the circumference of row 308d relative to the circumference of row 308c, the relationship of the circumference of row 308e relative to the circumference of row 308d, and the relationship of the circumference of row 308f relative to the circumference of row 308e, wherein the circumference of row 308f is larger than that of each of the other rows 308a-308e. Further, in this arrangement, the relative positioning of tear-drop shaped knobs 310 for each row 308a-308f is slightly offset. Thus, when valve 150' is viewed from valve opening 151', tear-drop shaped knobs 310 appear in a pin-wheel style configuration. This configuration advantageously minimizes electrostatic forces between the valve 150' and related instruments as the valve opening 151' is deformed temporarily by contact pressure from the tool 22, 23, 24, 25, wherein contact area between the valve 115' and the instruments is similarly reduced.

As constructed, for example, the valve 150' advantageously has a stretching or elastic range to readily accommodate, e.g., auto-reduction, tools or other instruments having a diameter of about 4 millimeters to about 15 millimeters as understood by those skilled in the art while still maintaining pneumoperitoneum. The valve opening 151' of the valve body 155' has a diameter less than the diameter of each of the tools 22, 23, 24, 25 that extend through the valve 150' so that a secured seal is provided around outer peripheries of each of the tools. With the valve 150' and second valve 160, in combination, the trocar system 120 advantageously can receive different diameter instruments without the necessity of switching cannulas or valve systems. This stretching or elastic range is not hampered by the plurality of protrusions 302, wherein the preferred arrangement and configuration thereof, as described, serves to facilitate the insertion and removal of instruments without loss of performance relative to accommodation of and sealing about the range of instrument diameters discussed. The valve 150' is advantageously fixedly secured to the valve housing 132 in the same manner as the valve 150, as exemplarily illustrated in FIG. 23.

As noted, the preferred tear-drop shaped knobs 310 serve to facilitate the manufacturing process, wherein successful formation and ejection of valve 150' from a mold is achieved more readily relative other shapes for knobs 310. Thus, while it is recognized that other shapes could be utilized, the preferred tear-drop shape is preferred. Further, while the arrangement of plurality of protrusions 302 is depicted and described according to the preferred configuration, wherein a particular roughness quality is achieved, relative to frictional force, other arrangements could be utilized, including more rows, aligned rows, non-rows and/or an arrangement of protrusions with close relative proximity, even approaching or achieving an essentially solid configuration, such as an annular rib; however, resulting modification to the roughness and/or related electrostatic nature of the surface could influence the achieved performance enhancement relative to the preferred configuration.

In the drawings and specification, there have been disclosed a typical preferred embodiment of the invention, and although specific terms are employed, the terms are used in descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

We claim:

1. A cap assembly of a cannula comprising:
a valve housing having at least one opening formed in line with an axis of said valve housing, said at least one opening being defined by an inner valve housing sidewall; and
a first valve positioned at least partially within said valve housing and including a valve body having:
a proximal valve section positioned within said valve housing and including an annular shaped valve ring having a proximal surface, a distal surface, an inner perimeter surface, and an outer perimeter surface,
a distal valve section extending axially from said proximal valve section and including a valve extension having a proximal end portion, a distal end portion, and a substantially conically shaped medial portion connected to and extending therebetween, and having a plurality of friction-reduction features disposed proximate said distal end portion and extending a distance in said substantially conically shaped medial portion; and a valve opening positioned in said distal end portion of said valve extension and adapted to individually and separately receive therethrough any one of a plurality of different elongate tools each having a different diameter so that when any one of the plurality of elongate tools is positioned through said valve opening a seal is maintained between peripheries of said valve extension surrounding said valve opening and outer peripheries of any one of plurality of elongate tools extending therethrough, wherein said proximal valve section, said distal valve section, and said valve opening comprise said valve body, and wherein said valve body is a singularly formed member.

2. A cap assembly as defined in claim 1,
wherein said plurality of friction-reduction features disposed proximate said distal end portion and extending a distance in said substantially conically shaped medial portion of said valve extension comprise a plurality of protrusions extending from a first outer surface of said valve extension and a plurality of protrusions extending from a second, opposing inner surface of said valve extension.

3. A cap assembly as defined in claim 2,
wherein said plurality of protrusions comprise tear-drop shaped knobs.

4. A cap assembly as defined in claim 1,
wherein said plurality of friction-reduction features disposed proximate said distal end portion and extending a distance in said substantially conically shaped medial portion of said valve extension comprise a plurality of protrusions extending from a first outer surface of said valve extension and a plurality of protrusions extending from a second, opposing inner surface of said valve extension, said plurality of protrusions defining a plurality of annular-shaped rows circumferentially surrounding said annular-shaped valve opening.

5. A cap assembly as defined in claim 4,
wherein said plurality of protrusions of each said annular-shaped row of said plurality of annular-shaped rows is offset relative to each said adjacent annular-shaped row.

6. A cap assembly as defined in claim 2,
wherein said plurality of protrusions define a pinwheel-shaped surface pattern, and
wherein a center of said pinwheel-shaped surface pattern is said annual-shaped valve opening.

7. A cap assembly as defined in claim 1,
wherein said inner valve housing sidewall extends distally in a substantially axial direction, and
wherein said valve housing further comprises:
a proximal end housing portion including a first opening having a first opening diameter defined by portions of said inner valve housing sidewall extending distally in said substantially axial direction, and an annular valve ring recess surrounding said inner valve housing sidewall and said first opening positioned to receive said annular shaped valve ring;
a distal end housing portion including a second opening having a second opening diameter defined by a distal valve housing sidewall extending in a substantially axial direction; and
a medial housing portion connected to and extending between said proximal end housing portion and said distal end housing portion and having a proximal valve housing inner perimeter surface and a distal valve housing inner perimeter surface.

8. A cap assembly as defined in claim 1,
wherein said ring housing has a valve ring recess,
wherein said valve ring is positioned in the valve ring recess, and
wherein said cap assembly further comprises a compression ring positioned in said valve housing abuttingly contacting an axially facing distal surface of said valve ring to hold said valve ring in said valve ring recess and to compress said valve ring against an axially facing inner surface of said proximal end housing portion of said valve housing adjacent said valve ring recess in order to fixedly position said valve at least partially within said valve housing.

9. A cap assembly as defined in claim 1,
wherein said valve housing includes a valve housing inner perimeter surface,
wherein said proximal valve section of said valve body further includes a plurality of convolutes each having a convolute recess, and
wherein said cap assembly includes compression ring including:
a compression ring opening substantially aligned axially with said at least one opening of said valve housing to allow extension of said plurality of elongate tools therethrough;
an outer perimeter surface having a radial diameter sized so that said compression ring substantially abuttingly contacts said valve housing inner perimeter surface and said distal surface of said valve ring when positioned within said valve housing; and
a flange extending into at least one of said plurality of convolute recesses to rigidly hold said valve ring within said valve housing.

10. A cap assembly as defined in claim 1,
wherein said proximal valve section of said valve body further includes:
a plurality of convolutes each having a first sidewall extending radially inwardly from a portion of said inner perimeter surface of said valve ring, and a second sidewall extending axially from said first sidewall substantially parallel to said inner perimeter surface of said valve ring and forming an inner radial periphery of the proximal valve section, said inner perimeter surface of said valve ring, said first sidewall, and said second sidewall of each of said plurality of convolutes forming a respective convolute recess for each of said plurality of convolutes; and
a plurality of rib members each radially extending substantially an entire distance between said inner radial periphery of said proximal valve section and inner perimeter surface of said valve ring and symmetrically positioned spaced-apart from each other.

11. A cap assembly as defined in claim 10,
wherein said plurality of convolutes are each positioned between and connected to two adjacent rib members;
wherein said cap assembly further comprises a compression ring positioned in said valve housing abuttingly contacting an axially facing distal surface of said valve ring to hold said valve ring in said valve housing, said compression ring including a compression ring opening substantially aligned axially with said at least one opening of said valve housing to allow extension of the plurality of elongate tools therethrough, and at least one flange extending into at least one of the plurality of convolute recesses;

wherein said at least one flange extending into at least one of said plurality of convolute recesses includes a plurality of notches positioned spaced-apart from each other to align with said plurality of rib members of said proximal valve section of said valve body to thereby rotationally align said compression ring with said valve ring when positioned in contact therewith; and wherein each of said plurality of notches receives a separate one of said plurality of rib members to prevent rotational movement of said proximal valve section.

12. A cap assembly as defined in claim 1, wherein said valve positioned at least partially within said valve housing is a first valve, wherein said at least one opening of said valve housing includes a first opening having a first opening diameter defined by portions of an inner valve housing sidewall extending distally in a substantially axial direction and a second opening having a second opening diameter defined by a distal valve housing sidewall extending in a substantially axial direction having a distal valve inner housing perimeter surface, and wherein said cap assembly further includes a second valve positioned adjacent said second opening of said valve housing, said second valve comprising:

an annular flange portion spaced axially from said valve ring of said first valve and having a radial diameter sized so that said annular flange portion substantially abuttingly contacts said distal valve inner housing perimeter surface to enhance positioning of said second valve at least partially within the valve housing;

a second valve opening positioned within said annular flange portion and substantially aligned axially with a first opening of valve housing to allow extension of the plurality of elongate tools therethrough;

an annular-shaped sidewall connected to said annular flange and extending distally in a substantially axial direction when positioned in said valve housing; and a pair of valve flaps connected to and extending inwardly from said annular-shaped sidewall and having at least one slit along common peripheral edges thereof through which the plurality of tools extend individually and separately.

13. A cap assembly as defined in claim 12, further comprising a cap seal ring positioned at least partially within said valve housing and abuttingly contacting a distal surface of said annular flange portion of said second valve, said cap seal ring also including at least one radially extending flange adapted to engage outer peripheries of a proximal portion of a cannula to detachably connect said valve housing to the cannula.

14. A cap assembly as defined in claim 2, wherein each said protrusion of said plurality of protrusions is of a shape selected from the group consisting of: tear-drop, circular, spherical, and annular rib shapes.

* * * * *